(12) United States Patent
Maltbie et al.

(10) Patent No.: US 9,491,236 B2
(45) Date of Patent: Nov. 8, 2016

(54) SYSTEM AND METHOD FOR SECURE, HIGH-SPEED TRANSFER OF VERY LARGE FILES

(71) Applicant: ANNAI SYSTEMS, INC., Carlsbad, CA (US)

(72) Inventors: Daniel Maltbie, Sunnyvale, CA (US); Lawrence Ganeshalingam, Los Gatos, CA (US); Patrick Allen, Scotts Valley, CA (US)

(73) Assignee: ANNAI SYSTEMS INC.

( * ) Notice: Subject to any disclaimer, the term of this patent is extended or adjusted under 35 U.S.C. 154(b) by 98 days.

(21) Appl. No.: 13/925,748

(22) Filed: Jun. 24, 2013

(65) Prior Publication Data

US 2014/0164516 A1    Jun. 12, 2014

Related U.S. Application Data

(60) Provisional application No. 61/662,996, filed on Jun. 22, 2012.

(51) Int. Cl.
  *G06F 15/16*  (2006.01)
  *H04L 29/08*  (2006.01)
  *G06F 19/28*  (2011.01)

(52) U.S. Cl.
  CPC ............ *H04L 67/104* (2013.01); *G06F 19/28* (2013.01); *H04L 67/06* (2013.01); *H04L 67/108* (2013.01); *H04L 67/1063* (2013.01)

(58) Field of Classification Search
  CPC ................... H04L 2209/60; H04L 67/1063
  USPC .................................................. 709/203, 204
  See application file for complete search history.

(56) References Cited

U.S. PATENT DOCUMENTS

| | | | |
|---|---|---|---|
| 5,668,810 A | 9/1997 | Cannella, Jr. |
| 6,119,120 A | 9/2000 | Miller |
| 6,582,932 B1 | 6/2003 | Fukiage et al. |
| 6,920,396 B1 | 7/2005 | Wallace et al. |
| 7,158,892 B2 | 1/2007 | Robson et al. |
| 7,248,582 B2 | 7/2007 | Belgaied et al. |
| 7,292,709 B2 | 11/2007 | Imajo |
| 7,354,720 B2 | 4/2008 | Cuppoletti et al. |
| 7,359,379 B2 | 4/2008 | Jarabek et al. |

(Continued)

FOREIGN PATENT DOCUMENTS

| EP | 0429201 | 5/1991 |
|---|---|---|
| KR | 10-2007-0115964 | 12/2007 |

(Continued)

OTHER PUBLICATIONS

Office Action for U.S. Appl. No. 12/828,234, mailed May 22, 2012.

(Continued)

*Primary Examiner* — Adnan Mirza
(74) *Attorney, Agent, or Firm* — Cooley LLP

(57) ABSTRACT

A method for parallelized transfer of an electronic file over a network. The method includes sending a first portion of the electronic file from a first sending node and receiving, at the first sending node, information relating to a second portion of the electronic file sent by a second sending node. The method further includes sending a third portion of the electronic file from the first sending node, wherein the third portion is different from the second portion.

25 Claims, 19 Drawing Sheets

(56) References Cited

U.S. PATENT DOCUMENTS

| | | | |
|---|---|---|---|
| 7,366,352 | B2 | 4/2008 | Kravec et al. |
| 7,408,957 | B2 | 8/2008 | Calvignac et al. |
| 7,428,554 | B1 | 9/2008 | Coberley et al. |
| 7,467,219 | B2 | 12/2008 | Hodges et al. |
| 7,739,390 | B2 | 6/2010 | Brahmbhatt et al. |
| 7,820,378 | B2 | 10/2010 | van den Boom et al. |
| 7,856,317 | B2 | 12/2010 | Schilling |
| 7,885,969 | B2 | 2/2011 | Natarajan et al. |
| 7,996,876 | B1 | 8/2011 | Everson et al. |
| 8,412,462 | B1 | 4/2013 | Ganeshalingam et al. |
| 8,606,846 | B2 | 12/2013 | Czechowski, III et al. |
| 8,982,879 | B2 | 3/2015 | Ganeshalingam et al. |
| 2002/0029113 | A1 | 3/2002 | Wang et al. |
| 2002/0103937 | A1 | 8/2002 | Tillmann et al. |
| 2002/0111742 | A1 | 8/2002 | Rocke et al. |
| 2003/0039362 | A1 | 2/2003 | Califano et al. |
| 2003/0055824 | A1 | 3/2003 | Califano et al. |
| 2003/0082544 | A1 | 5/2003 | Fors et al. |
| 2003/0097227 | A1 | 5/2003 | Bloch et al. |
| 2003/0113756 | A1 | 6/2003 | Mertz |
| 2003/0224419 | A1 | 12/2003 | Corcoran et al. |
| 2003/0236393 | A1 | 12/2003 | Trucksis |
| 2004/0003132 | A1* | 1/2004 | Stanley et al. ............... 709/316 |
| 2004/0005558 | A1 | 1/2004 | Anderson et al. |
| 2004/0006433 | A1 | 1/2004 | Robson et al. |
| 2005/0049795 | A1 | 3/2005 | Fikuda et al. |
| 2005/0053968 | A1 | 3/2005 | Bharadwaj et al. |
| 2005/0060599 | A1 | 3/2005 | Inami et al. |
| 2005/0075794 | A1 | 4/2005 | Hoffman et al. |
| 2005/0119535 | A1 | 6/2005 | Yanagihara et al. |
| 2005/0131649 | A1 | 6/2005 | Larsen et al. |
| 2005/0164247 | A1 | 7/2005 | Brunkow et al. |
| 2005/0181362 | A1 | 8/2005 | Apolito et al. |
| 2005/0267693 | A1 | 12/2005 | Allard et al. |
| 2005/0267971 | A1 | 12/2005 | Fritz |
| 2006/0224687 | A1 | 10/2006 | Popkin et al. |
| 2006/0285685 | A1 | 12/2006 | Msezane |
| 2007/0026406 | A1 | 2/2007 | El Ghaoui et al. |
| 2007/0042372 | A1 | 2/2007 | Arita |
| 2007/0101154 | A1 | 5/2007 | Bardsley et al. |
| 2007/0148658 | A1 | 6/2007 | Nelson et al. |
| 2007/0168135 | A1 | 7/2007 | Agarwal et al. |
| 2007/0190534 | A1 | 8/2007 | Birch-Machin et al. |
| 2007/0271604 | A1 | 11/2007 | Webster et al. |
| 2007/0288172 | A1 | 12/2007 | Aronow et al. |
| 2008/0016201 | A1 | 1/2008 | Thompson |
| 2008/0077607 | A1 | 3/2008 | Gatawood et al. |
| 2008/0255877 | A1 | 10/2008 | Fernandez |
| 2008/0271053 | A1 | 10/2008 | Kramer et al. |
| 2008/0281818 | A1 | 11/2008 | Tenenbaum et al. |
| 2009/0203986 | A1 | 8/2009 | Winnick |
| 2010/0014496 | A1 | 1/2010 | Kalika et al. |
| 2010/0050253 | A1 | 2/2010 | Baughman et al. |
| 2010/0135488 | A1* | 6/2010 | Lee et al. ............... 380/200 |
| 2010/0161607 | A1 | 6/2010 | Singh et al. |
| 2010/0169107 | A1 | 7/2010 | Ahn et al. |
| 2010/0169313 | A1 | 7/2010 | Kenedy et al. |
| 2010/0169338 | A1 | 7/2010 | Kenedy et al. |
| 2010/0169340 | A1 | 7/2010 | Kenedy et al. |
| 2010/0262718 | A1 | 10/2010 | Ikeno et al. |
| 2012/0047202 | A1 | 2/2012 | Van Ackere et al. |
| 2012/0089339 | A1 | 4/2012 | Ganeshalingam et al. |
| 2012/0089603 | A1 | 4/2012 | Ganeshalingam et al. |
| 2012/0089607 | A1 | 4/2012 | Ganeshalingam et al. |
| 2012/0089608 | A1 | 4/2012 | Ganeshalingam et al. |
| 2012/0089652 | A1 | 4/2012 | Ganeshalingam et al. |
| 2012/0095693 | A1 | 4/2012 | Ganeshalingam et al. |
| 2012/0230326 | A1 | 9/2012 | Ganeshalingam et al. |
| 2012/0230338 | A1 | 9/2012 | Ganeshalingam et al. |
| 2012/0230339 | A1 | 9/2012 | Ganeshalingam et al. |
| 2012/0232874 | A1 | 9/2012 | Ganeshalingam et al. |
| 2012/0233201 | A1 | 9/2012 | Ganeshalingam et al. |
| 2012/0233202 | A1 | 9/2012 | Ganeshalingam et al. |
| 2012/0236861 | A1 | 9/2012 | Ganeshalingam et al. |
| 2013/0246460 | A1 | 9/2013 | Maltbie et al. |
| 2014/0164515 | A1 | 6/2014 | Maltbie et al. |

FOREIGN PATENT DOCUMENTS

| | | |
|---|---|---|
| WO | WO 97/22076 | 6/1997 |
| WO | WO 2004/015579 | 2/2004 |
| WO | WO 2006/084391 | 8/2006 |
| WO | WO 2006/102128 | 9/2006 |

OTHER PUBLICATIONS

Office Action for U.S. Appl. No. 12/828,234, mailed Mar. 13, 2013.
Office Action for U.S. Appl. No. 12/837,452, mailed Apr. 5, 2012.
Office Action for U.S. Appl. No. 13/223,071, mailed Nov. 13, 2013.
International Search Report and Written Opinion for International Application No. PCT/US2011/050073, mailed Apr. 25, 2012.
Office Action for U.S. Appl. No. 13/223,077, mailed Nov. 20, 2012.
International Search Report and Written Opinion for International Application No. PCT/US2011/050075, mailed Apr. 25, 2012.
Office Action for U.S. Appl. No. 13/223,084, mailed May 12, 2014.
Office Action for U.S. Appl. No. 13/223,084, mailed Sep. 27, 2013.
Office Action for U.S. Appl. No. 13/223,084, mailed Feb. 7, 2013.
International Search Report and Written Opinion for International Application No. PCT/US2011/050077, mailed Apr. 27, 2012.
Office Action for U.S. Appl. No. 13/223,088, mailed Jan. 2, 2013.
International Search Report and Written Opinion for International Application No. PCT/US2011/050078, mailed Mar. 21, 2012.
Office Action for U.S. Appl. No. 13/223,092, mailed May 12, 2014.
Office Action for U.S. Appl. No. 13/223,092, mailed Sep. 6, 2013.
Office Action for U.S. Appl. No. 13/223,092, mailed Feb. 7, 2013.
International Search Report and Written Opinion for International Application No. PCT/US2011/050079, mailed Apr. 9, 2012.
Office Action for U.S. Appl. No. 13/223,097, mailed Sep. 18, 2013.
Office Action for U.S. Appl. No. 13/223,097, mailed Nov. 16, 2012.
International Search Report and Written Opinion for International Application No. PCT/US2011/050080, mailed May 1, 2012.
Office Action for U.S. Appl. No. 13/290,992, mailed Sep. 13, 2013.
Office Action for U.S. Appl. No. 13/417,184, mailed Nov. 26, 2013.
International Search Report and Written Opinion for International Application No. PCT/US2012/028642, mailed Oct. 23, 2012.
International Search Report and Written Opinion for International Application No. PCT/US2012/028643, mailed Sep. 3, 2012.
Office Action for U.S. Appl. No. 13/417,188, mailed Nov. 4, 2013.
International Search Report and Written Opinion for International Application No. PCT/US2012/028644, mailed Sep. 3, 2012.
Office Action for U.S. Appl. No. 13/417,189, mailed Nov. 4, 2013.
International Search Report and Written Opinion for International Application No. PCT/US2012/028645, mailed Sep. 3, 2012.
Office Action for U.S. Appl. No. 13/417,190, mailed Nov. 29, 2013.
International Search Report and Written Opinion for International Application No. PCT/US2012/028647, mailed Sep. 26, 2012.
Office Action for U.S. Appl. No. 13/417,192, mailed Mar. 26, 2014.
Office Action for U.S. Appl. No. 13/417,192, mailed Aug. 30, 3013.
International Search Report and Written Opinion for International Application No. PCT/US2012/028650, mailed Sep. 27, 2012.
Office Action for U.S. Appl. No. 13/417,193, mailed Feb. 13, 2014.
Office Action for U.S. Appl. No. 13/417,193, mailed May 23, 2013.
International Search Report and Written Opinion for International Application No. PCT/US2012/028652, mailed Oct. 23, 2012.
International Search Report and Written Opinion for International Application No. PCT/US2012/057668, mailed Jan. 17, 2013.
International Search Report and Written Opinion for International Application No. PCT/US2013/047438, mailed Nov. 1, 2013.
Calabretta, N. et al., "Optical Signal Processing Based on Self-Induced Polarization Rotation in a Semiconductor Optical Amplifier," Journal of Lightwave Technology, 22(2):372-381 (Feb. 2004).
UHN Human CpG Island Microarray Database Searches [online], Retrieved from the Internet on Sep. 28, 2011 and Oct. 3, 2011, <URL: http://data.microarrays.ca/cpg/index.htm>, 16 pages.

(56) References Cited

OTHER PUBLICATIONS

Tanenbaum, D. M. et al., "The JCVI Standard Operating Procedure for Annotating Prokaryotic Metagenmic Shotgun Sequencing Data," Standards in Genomic Sciences, 2(2):229-237 (Apr. 2010).
International Preliminary Report on Patentability for International Application No. PCT/US2011/050073, mailed Mar. 5, 2013.
International Preliminary Report on Patentability for International Application No. PCT/US2011/050075, mailed Mar. 5, 2013.
International Preliminary Report on Patentability for International Application No. PCT/US2011/050077, mailed Mar. 5, 2013.
International Preliminary Report on Patentability for International Application No. PCT/US2011/050078, mailed Mar. 5, 2013.
International Preliminary Report on Patentability for International Application No. PCT/US2011/050079, mailed Mar. 5, 2013.
International Preliminary Report on Patentability for International Application No. PCT/US2011/050080, mailed Mar. 5, 2013.
International Preliminary Report on Patentability for International Application No. PCT/US2012/028642, mailed Sep. 10, 2013.
International Preliminary Report on Patentability for International Application No. PCT/US2012/028643, mailed Sep. 10, 2013.
International Preliminary Report on Patentability for International Application No. PCT/US2012/028644, mailed Sep. 10, 2013.
International Preliminary Report on Patentability for International Application No. PCT/US2012/028645, mailed Sep. 10, 2013.
International Preliminary Report on Patentability for International Application No. PCT/US2012/028647, mailed Sep. 10, 2013.
International Preliminary Report on Patentability for International Application No. PCT/US2012/028650, mailed Sep. 10, 2013.
International Preliminary Report on Patentability for International Application No. PCT/US2012/028652, mailed Sep. 10, 2013.
International Preliminary Report on Patentability for International Application No. PCT/US2012/057668, mailed Apr. 1, 2014.
International Preliminary Report on Patentability for International Application No. PCT/US2013/047438, mailed Dec. 23, 2014.
Office Action for U.S. Appl. No. 13/223,084, mailed Mar. 23, 2015, 11 pages.
Office Action for U.S. Appl. No. 13/925,747, mailed Apr. 14, 2015, 9 pages.
Office Action for U.S. Appl. No. 13/417,189, mailed May 14, 2015, 11 pages.
Notice of Allowance for U.S. Appl. No. 13/417,192, mailed Jun. 9, 2015, 7 pages.
Office Action for U.S. Appl. No. 13/417,184, mailed Jun. 24, 2015, 10 pages.
Office Action for U.S. Appl. No. 12/828,234, mailed Sep. 8, 2014, 32 pages.
Office Action for U.S. Appl. No. 13/223,071, mailed Jun. 5, 2014, 15 pages.
Office Action for U.S. Appl. No. 13/223,071, mailed Dec. 26, 2014, 14 pages.
Office Action for U.S. Appl. No. 13/223,084, mailed Aug. 6, 2014, 10 pages.
Office Action for U.S. Appl. No. 13/223,092, mailed Jun. 25, 2014, 9 pages.
Office Action for U.S. Appl. No. 13/223,092, mailed Jan. 16, 2015, 14 pages.
Office Action for U.S. Appl. No. 13/223,097, mailed Jun. 5, 2014, 8 pages.
Office Action for U.S. Appl. No. 13/223,097, mailed Jan. 7, 2015, 14 pages.
Office Action for U.S. Appl. No. 13/290,992, mailed Aug. 29, 2014, 15 pages.
Office Action for U.S. Appl. No. 13/290,992, mailed Jan. 7, 2015, 11 pages.
Office Action for U.S. Appl. No. 13/417,184, mailed Jun. 16, 2014, 11 pages.
Office Action for U.S. Appl. No. 13/417,187, mailed May 21, 2014, 12 pages.
Office Action for U.S. Appl. No. 13/417,187, mailed Dec. 23, 2014, 13 pages.
Office Action for U.S. Appl. No. 13/417,188, mailed May 29, 2014, 9 pages.
Office Action for U.S. Appl. No. 13/417,189, mailed May 27, 2014, 9 pages.
Office Action for U.S. Appl. No. 13/417,190, mailed Aug. 29, 2014, 10 pages.
Office Action for U.S. Appl. No. 13/417,192, mailed Nov. 19, 2014, 11 pages.
Office Action for U.S. Appl. No. 13/417,193, mailed Sep. 11, 2014, 43 pages.
Networking Tutorial, The CTDP Networking Guide, Version 0.6.3 (Feb. 3, 2001), pp. 1-149.

\* cited by examiner

SYSTEM AND METHOD FOR SECURE, HIGH-SPEED TRANSFER OF VERY LARGE FILES

CROSS-REFERENCE TO RELATED APPLICATIONS

The present application claims the benefit of priority under 35 U.S.C. §119(e) of U.S. Provisional Application Ser. No. 61/662,996, entitled SYSTEM AND METHOD FOR SECURE, HIGH-SPEED TRANSFER OF VERY LARGE FILES, filed Jun. 22, 2012, the contents of which is hereby incorporated by reference in its entirety for all purposes.

FIELD

This disclosure generally relates to the transfer of files of large size, and more particularly relates to systems and methods for the secure and high-speed transfer of such files.

BACKGROUND

The transmission control protocol ("TCP") is known to use the additive increase/multiplicative decrease algorithm to avoid congestion and control bandwidth usage. Unfortunately, this aspect of TCP can impede the transmission rate of very large sequence data files, even on high-speed networks.

A "peer-to-peer" network of computers harnesses the bandwidth and computational power of the computers participating in the network. This contrasts with conventional "client-server" approaches, in which computing power and bandwidth are concentrated in a relatively small number of servers. Such peer-to-peer networks may facilitate the transfer of files through a set of connections established between participating peers.

BitTorrent is a popular file distribution program currently used in peer-to-peer networks. A peer within a BitTorrent system may be any computer running an instance of a client program implementing the BitTorrent protocol. Each BitTorrent client is capable of preparing, requesting, and transmitting any type of computer file over a network in accordance with the BitTorrent protocol. BitTorrent is designed to enable distribution of large amounts of data without consuming correspondingly large amounts of computational and bandwidth resources.

To share a file or group of files, a BitTorrent peer first creates a small file called a "torrent" (e.g. "Filename.torrent"). The torrent file contains metadata about the files to be shared and also includes information about a component, termed the "tracker", that coordinates the file distribution. Torrent files are generally published on a website or other accessible network location. The tracker maintains lists of the clients currently participating in the torrent. A peer desiring to download a file of interest must first obtain a copy of the corresponding torrent file and connect to the specified tracker. The tracker then informs the peer from which other peers pieces of the file of interest may be downloaded.

The peer distributing a data file generally treats the file as being comprised of a number of identically-sized pieces, usually with byte sizes of a power of 2, and typically between 32 kB and 16 MB each. The peer creates a hash for each piece, using the SHA-1 hash function, and records the hash value in the torrent file. When another peer later receives a particular piece, the hash of the piece is compared to the recorded hash to test that the piece is free of errors. Peers that provide a complete file are called "seeders", and the peer providing the initial copy of the file may be called the "initial seeder".

The exact information contained in the torrent file depends on the version of the BitTorrent protocol being utilized. In general, torrent files include an "announce" section, which specifies the URL of the tracker. Torrent files also include an "info" section, which contains suggested names for the files, their respective lengths, the piece length used, and a SHA-1 hash code for each piece. This information is used by requesting peers to verify the integrity of the data received.

With respect to a given file, the tracker maintains records of which peers are "seeds" (i.e., a peer having the complete file(s) being distributed) and of the other peers in the applicable "swarm" (i.e., the set of seeds and peers involved in the distribution of the file(s)). During the distribution process peers periodically report information to the tracker and request and receive information concerning other peers to which they may connect. Users interested in obtaining a file or files using BitTorrent may, using a web browser installed on a local machine, navigate to a website listing the torrent and download it. Once downloaded, the torrent may be opened in a BitTorrent client stored on the local machine. Once the torrent is opened, the BitTorrent client establishes a connection with the tracker. At this point the tracker provides the BitTorrent client with a list of peers currently downloading the file or files of interest.

If a BitTorrent client happens to be the first such client interested in a file associated with a torrent, for at least some period of time such client may be the only peer within the swarm and thus connects directly to the initial seeder and requests pieces of the file. As other peers join the swarm, the peers exchange pieces with each other in addition to downloading pieces from the initial seeder.

Unfortunately, in the case of very large files it will generally be rather burdensome for the initial seeder to respond to requests for file pieces from multiple requesting peers. Moreover, limitations on the processing and input/output resources of the initial seeder may impede the efficient and rapid distribution of very large files.

SUMMARY

The present disclosure describes a system and method for secure, high-speed file transfer which is capable of overcoming the disadvantages of TCP and existing peer-to-peer protocols with respect to the distribution of files of very large size. Like other peer-to-peer file distribution systems, the disclosed GeneTorrent™ high-speed file transfer system utilizes a tracker to enable a plurality of peers to cooperatively distribute a file of interest. However, in one aspect the GeneTorrent™ system incorporates a Transactor which is integrated within or otherwise operates in conjunction with the tracker. The Transactor is a program which operates to immediately identify and make a record of those clients (i.e., actors) which request a certain file of interest (e.g., "file X"). The Transactor will also generally be configured to determine the authentication and entitlement of each actor based on authorization rules and using a secure key distribution scheme.

In one embodiment the Transactor clusters individual actors which have requested file X into a cast of participating actors comprising an affinity group. The Transactor may determine which actors are assigned to a particular cast based upon, for example, the file requested, the location of the file (i.e., with which actor(s) the file is currently stored), as well as the credentials of the actors requesting access to the file. Once an actor has been directed to a particular cast, the actor exchanges messages with other actors within the cast in order to determine and receive the portions of the file of interest currently possessed by the cast. Stated differently, the Transactor proactively directs a requesting leecher actor to a feeder affinity group such that the leecher receives as much of the requested file as possible without, to the extent possible, incrementing the burden on the seed of file X.

In the case of very large files, such as files containing genomic or other biological sequence information, the GeneTorrent™ approach effectively "parallelizes" the transfer of file information and reduces the burden on the initial seed or seeds of file X. Moreover, the use of parallel streams within the GeneTorrent™ system minimizes the effect of a multiplicative decrease in the speed of any one stream resulting from the characteristics of TCP discussed above. Thus, use of the GeneTorrent™ approach may reduce the likelihood of bottlenecks developing around overburdened seed servers in connection with the transfer of very large data files.

The use of such parallel streams also enables the separate encryption of each individual file segment, thus obviating the need for re-encryption and retransmission of the entire file in the event of corruption of an individual segment. Particularly in the case of very large data files containing sensitive information (e.g., files containing genomic sequence information), this aspect of the GeneTorrent™ approach may offer considerable advantages relative to existing methods of file distribution.

In one aspect, the present disclosure relates to a method for facilitating transfer of an electronic file over a network. The method includes sending a first portion of the electronic file from a first sending node and receiving, at the first sending node, information relating to a second portion of the electronic file sent by a second sending node. The method further includes sending a third portion of the electronic file from the first sending node, wherein the third portion is different from the second portion.

In a related aspect the method may further include reading the first portion of the electronic file and the third portion of the electronic file from a database containing the electronic file. In addition, the method may further include providing, to the second sending node, information relating to the sending of the first portion of the electronic file. Moreover, the method may include receiving information relating to a fourth portion of the electronic file sent by a third sending node wherein the third portion is different from the fourth portion.

The disclosure also pertains to a method for facilitating transfer of an electronic file over a network. The method includes generating first encrypted file information by encrypting a first portion of the electronic file using first encryption information, wherein the first portion is associated with a first layer of a plurality of layers of information within the electronic file. The method further includes generating second encrypted file information by encrypting a second portion of the electronic file using second encryption information different from the first encryption information, wherein the second portion is associated with a second layer of the plurality of layers of information. In addition, the method includes sending the first encrypted file information from a first sending node and sending the second encrypted file information from a second sending node.

In a further aspect, the present disclosure is directed to a method for facilitating transfer of an electronic file over a network. The method includes receiving, from a first receiving node, a first portion of an electronic file sent by a first sending node. The method further includes receiving, from a second receiving node, a second portion of the electronic file sent by a second sending node.

BRIEF DESCRIPTION OF THE DRAWINGS

For a better understanding of the nature and objects of various embodiments of the invention, reference should be made to the following detailed description taken in conjunction with the accompanying drawings, wherein.

DETAILED DESCRIPTION OF EMBODIMENTS

Introduction

Figure 1:
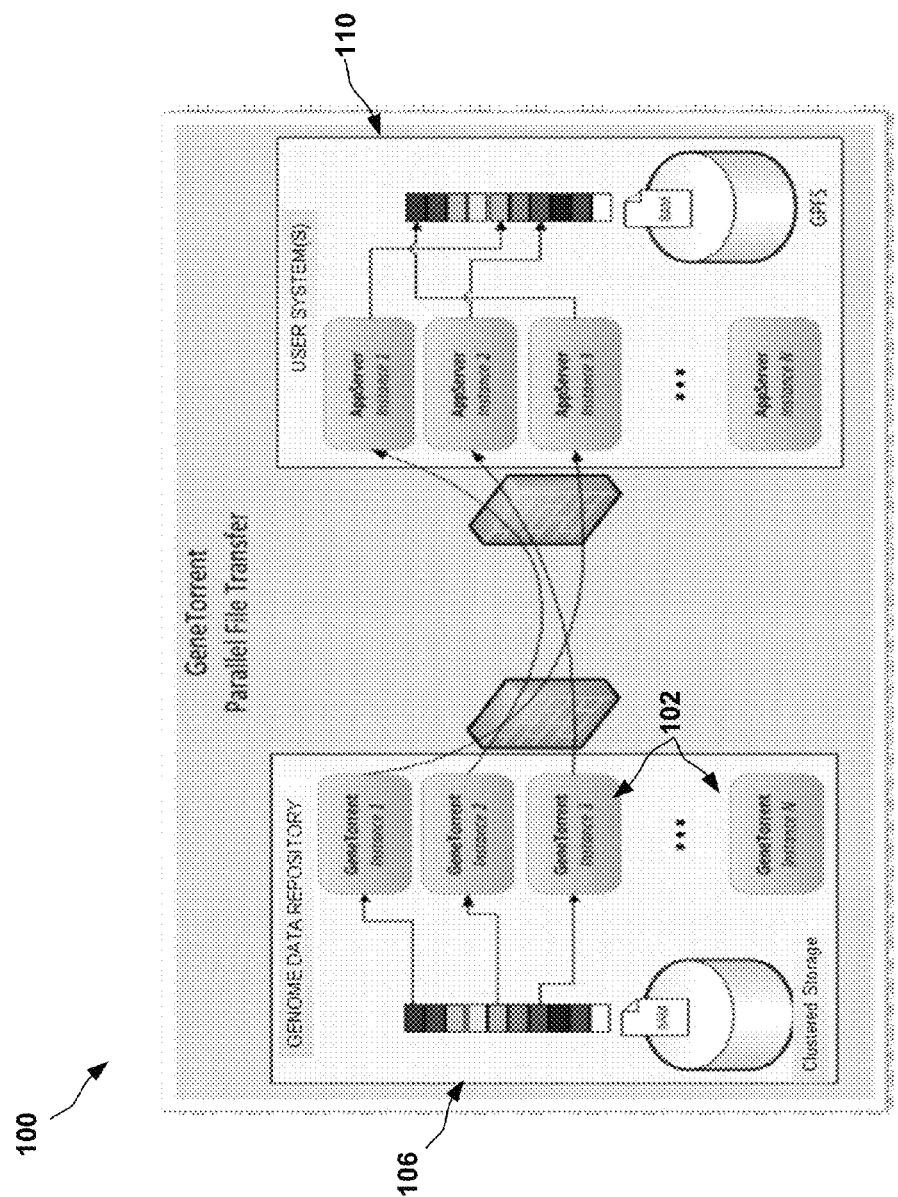
FIG. 1 provides a high-level representation of the architecture of a GeneTorrent™ system configured to form multiple instances of a GeneTorrent™ object file so as to enable a cluster of servers to tranfer parallel streams of file information to a user system.

At this early stage in the experimental development of the human genome biology and next generation sequencing (NGS) technology, there is yet still much to be discovered and understood.

For example, one major rate limiting step involves the ineffectiveness on the part of the research community to make decisions as a group to set the highest standards for the genomic data space. For example, it may be particularly important to develop standards around the quality of service that is used to touch genomic, transcriptomic, proteomic and other large volumes of omics data. Moreover, this type of biological data will typically require extreme security considerations. The dataset might contain genotypic and phenotypic information that could have profound effects on an individual if it is breached.

This information also requires special consideration with regards to data integrity and form; that is, the data need high-level validation. It is important that the data is transferred with the highest fidelity. In addition, these are very large datasets where failed transmissions can be costly in time.

Finally, some of this data will need to be conditionally accessible to different sources in various regions for various reasons. For example, if certain regions of the genome are required for breast cancer analysis the regions associated with other phenotypes and or diseases can remain inaccessible.

The approaches disclosed herein use a method to structure GeneTorrent™ Object ("GTO" or ".gto") files so as to allow multiple instances of parallelized streams to be sent and received by two or more actors. Consistent with the GeneTorrent™ protocol disclosed herein, very large biological sequence data files may be transferred at high-speed. In addition, security may be enhanced by applying encryption to parallel streams of N instances of the same GTO file from multiple servers. In one embodiment an entitlement control system may be used in conjunction with the GeneTorrent™ system to regulate authorization of actors and authentication for access to certain .gto files.

GeneTorrent™ Architecture & Characteristics

As is discussed below, in exemplary embodiments GeneTorrent™ system files are fragmented into pieces for parallel independent transfer. The location of multiple sources ("seeders") for a file may be advertised. In addition, actors or other peers may exchange protocol messages containing metadata about files. Exemplary embodiments of the GeneTorrent™ approach contemplate use of a number of unique techniques, including methods for limiting membership in the "swarm" of systems that can be "seeding" a file and requiring each pair of "actors" exchanging data to reciprocally authenticate. These novel techniques further include encrypting data in transit using strong, standard cryptographic technology and constraining peer-to-peer interactions to authenticated users with authorization to perform the requested "seeding" or "leeching" operations on the requested data.

In one embodiment user-level authentication and dataset authorization is performed before peers can initiate a GeneTorrent™ transfer. In this embodiment a GeneTorrent™ peer desiring to initiate a transfer first contacts a control component (hereinafter also termed a "GT Exec") on a GeneTorrent™ repository and passes the user credentials. The GT Exec authenticates that the credentials have not expired and correspond to a known user. The GT Exec may then further verify that the user is authorized to perform the requested action (e.g., upload or download) on the specific data files identified in the request.

GeneTorrent™ Object File Transfer—Multiple Parallel Streams

In one aspect GeneTorrent™ enables multiple sending actors to transfer file pieces to multiple receiving actors over parallel streams. This approach has several advantages. For example, parallel M:N transfers avoid many of the bottlenecks that occur in 1:1 transfers, such as issues with disk I/O, CPU utilization, large bandwidth-delay products in the WAN, and other side-effects of transferring very large data sets. Error detection and error recovery are built in, automatic and very robust. The protocol is content-agnostic, allowing data file formats to evolve without impacting the underlying transfer mechanisms The protocol scales asymmetrically—M:N transfers for high volume producers and 1:N downloaders for the periodic user are supported by the same application. The protocol is capable of saturating the available network bandwidth and reacts well to dynamic changes in the congestion levels in the transport network The GeneTorrent™ protocol is capable of rapidly and efficiently transmitting large biological sequence data files. As a result, in one embodiment a dynamic encryption key distribution system is integrated into the file transfer system to faciliate secure transfers. This allows for encryption of data in multiple layers that can be controlled using a hierarchical entitlement scheme. For example, one GTO file can be encrypted in a format that allows for multiple downloaders to access different layers of data from the files.

Attention is now directed to FIG. 1, which provides a high-level representation of the architecture of a GeneTorrent™ system 100 configured to form multiple instances of a GTO file so as to enable a cluster of servers 102 within or associated with a genome data respository (GDR) 106 to transfer parallel streams of file information to a user system 110. Although not shown in FIG. 1, integrated within or layered "on top of" the architecture is a higly secure encryption system.

Gene Torrent Object Files

In one embodiment an actor first locates a Torrent file describing the target data as an initial step in participating in a GeneTorrent™ parallel file transfer. Such a Torrent file may comprise a static "bencoded" dictionary including the Announce URL, an info dictionary, and other optional fields. In one embodiment GeneTorrent™ uses dynamic one-time Gene Torrent Object files to bootstrap a secure and encrypted file transfer based on bi-directionally authenticated SSL sessions.

In a GeneTorrent™ system, the Torrent file will generally be structured in order to accommodate the efficient transfer of very large files. For example, the task of generating the SHA1 hashes for all the "pieces" of a very large file would be computationally expensive and impose an unnecessary I/O burden on the local storage system. Accordingly, rather than regenerating new SHA1 hashes for every file piece each time a user downloads the file, in one embodiment one or more seeders cache the torrent data for reuse. Each large data file will have an associated static Torrent file which will be stored in the same directory. This torrent file may comprise a "normal" Torrent, i.e., it may lack SSL certificate information. Such certificate information and any other additional data fields may instead be dynamically inserted into the Gene Torrent Object file at the time of a download request, thus creating a one-time-use Torrent with authentication keys.

Transactor

As discussed above, the Transactor at least partially enables a GeneTorrent™ system to transmit a file of interest in multiple parallel streams to a requesting entity. As discussed above, in one embodiment the Transactor clusters individual actors which have requested file X into a cast of participating actors comprising an affinity group. The Transactor may determine which actors are assigned to a particular cast based upon, for example, the file requested, the location of the file (i.e., with which actor(s) the file is currently stored), as well as the credentials of the actors requesting access to the file. Once an actor has been directed to a particular cast, the actor exchanges messages with other actors within the cast in order to determine and receive the portions of the file of interest currently possessed by the cast. That is, a requesting leecher actor is proactively directed to a feeder affinity group such that the leecher receives as much of the requested file as possible without, to the extent possible, incrementing the burden on the seed of file X.

Figure 2:
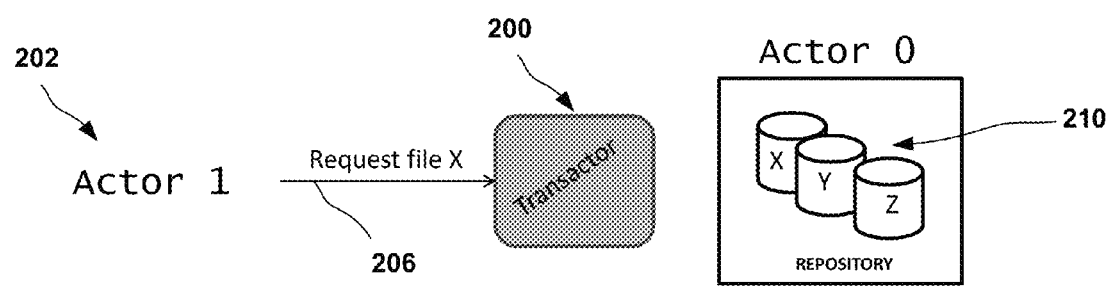
FIGS. 2-7 illustrate exemplary operation of one embodiment of a Transactor included within the GeneTorrent™ system.

Attention is now directed to FIGS. 2-7, which illustrate exemplary operation of one embodiment of a Transactor 200 within a GeneTorrent™ system. As shown in FIG. 2, a first Actor 202 ("Actor 1") makes a first request 206 to the GeneTorrent™ network for file X, such request being received by the Transactor 200. In the present example it is assumed that the only copy of file X is stored at a repository 210.

Figure 3:
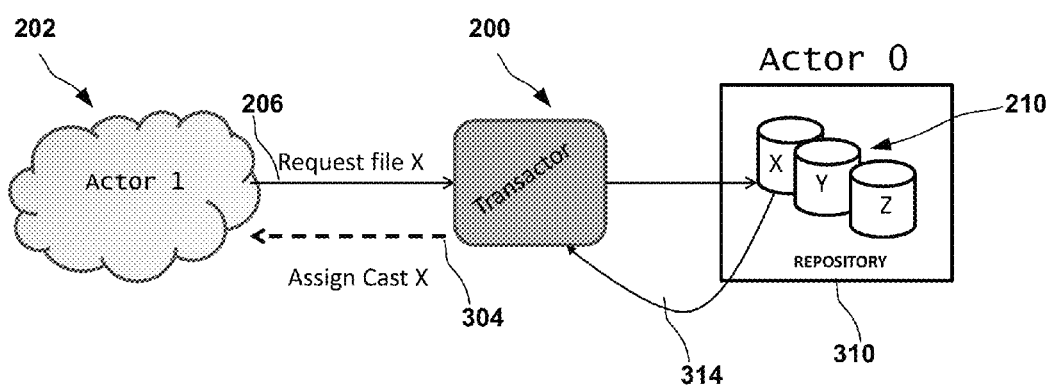

Referring to FIG. 3, the Transactor 200 then locates the actor(s) hosting file X on the network after authorization of Actor 1. Since the Transactor 200 has entitlement rights, Actor 1 is assigned 304 to the Cast X cluster. At this moment Actor 1 is the only actor in the Cast of X. Another Actor 310 ("Actor 0") prepares a GTO file and starts sending 314 random pieces of the file X to Actor 1.

Figure 4:
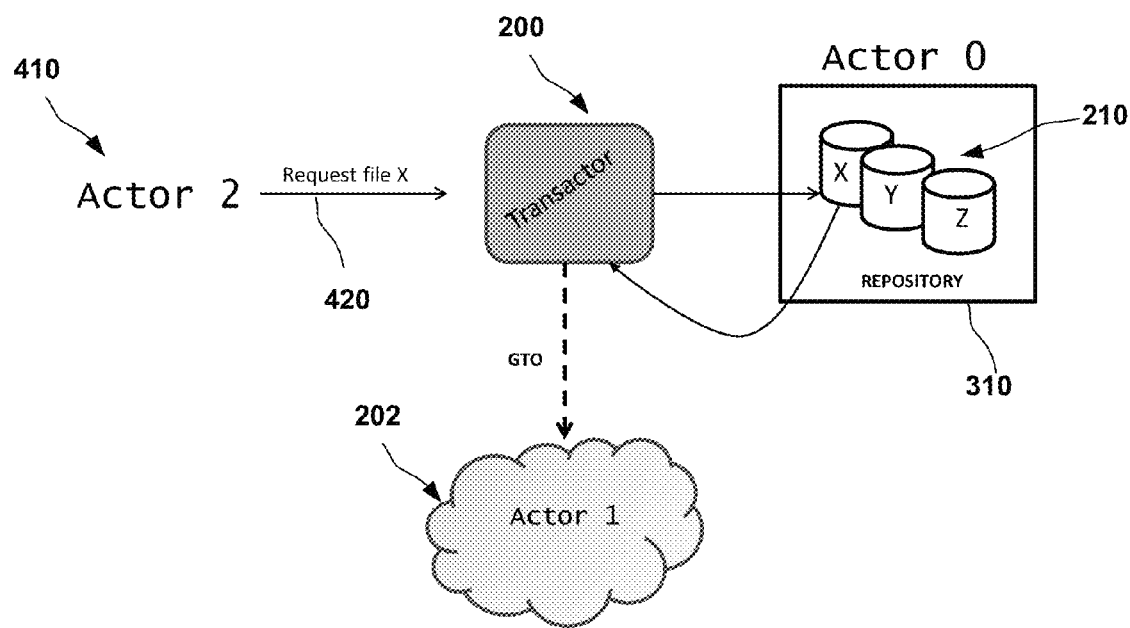

Turning now to FIG. 4, in the next moment an additional actor 410 ("Actor 2") makes a request 420 for file X. Because the Transactor 200 has access rights and is able to assign actors to a particular cast based on the file request, Actor 2 is immediately assigned to Cast X. By this assignment, the Transactor instructs Actor 2 to join Cast X and exchange messages with other actors in the cast in order to determine which parts of file X are possessed by the cast. At this point a GeneTorrent™ instance is initiated with those pieces of file X from Actor 1. Other pieces of the file X are received from either Actor 0 or Actor 1, which remain in communication with each other until the transmission request is complete.

Figure 5:
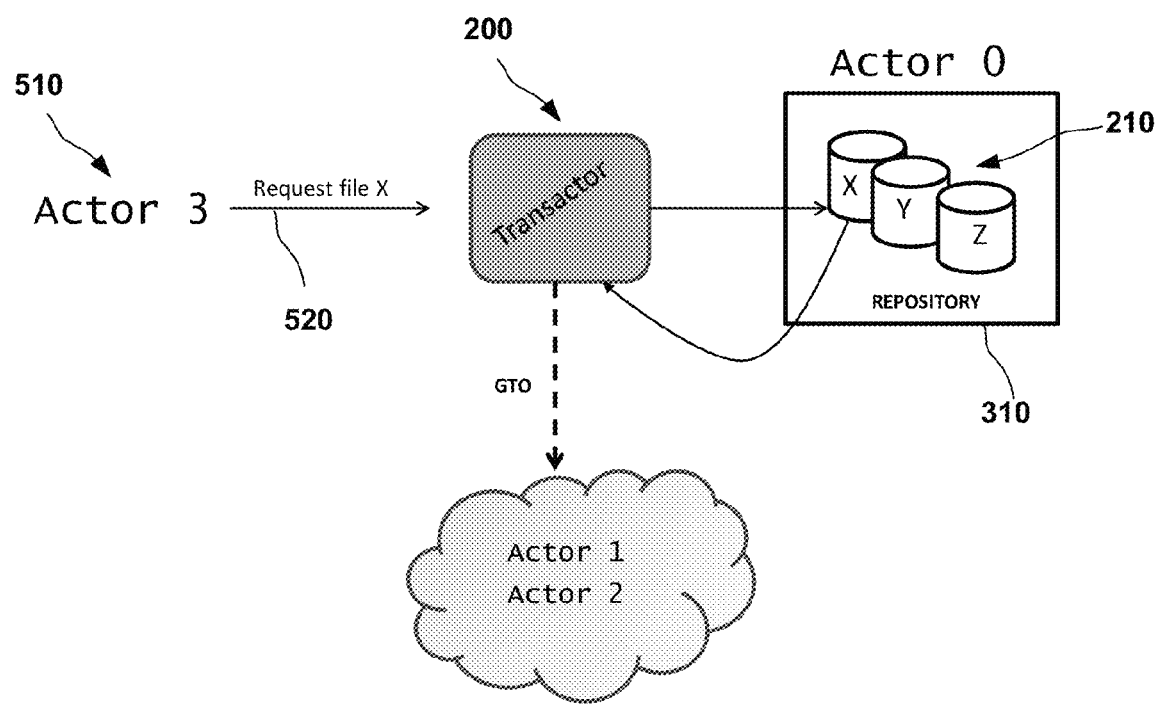

Referring to FIG. 5, a third actor 510 ("Actor 3") makes a request 520 for file X and is assigned by the Transactor 200 to the appropriate cast. At this point Actor 3 begins downloading those instances of file X that exist among the pool of actors in Cast X. The Transactor 200 is thus able to direct each actor to a related cast of actors so as to not overburden the original source of file X. That is, the Transactor 300 directs leechers to a feeder affinity group in order to obtain those portions of a file of interest available from the group without chokepoints.

Figure 6:
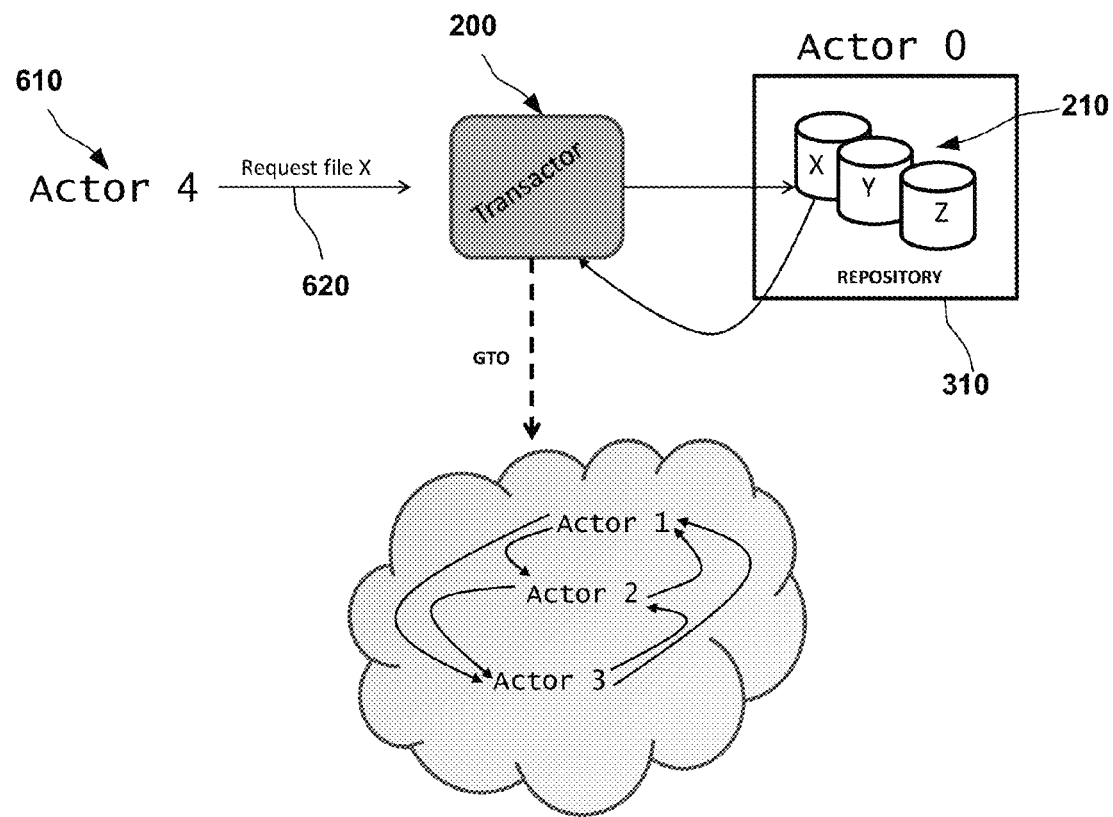

As represented by FIG. 6, a fourth actor 610 ("Actor 4") also makes a request 620 for file X. As is illustrated by FIG. 6, all actors in the cast, i.e., Actor 1, Actor 2 and Actor 3, may function as uploaders as well as downloaders at the same time since random pieces of the file X are being served among all cast members. Since in one embodiment authentication keys are distributed with the parallelized file transfer, all cast members can be confident that all instances of file X that are served among members are from the original source repository.

Figure 7:
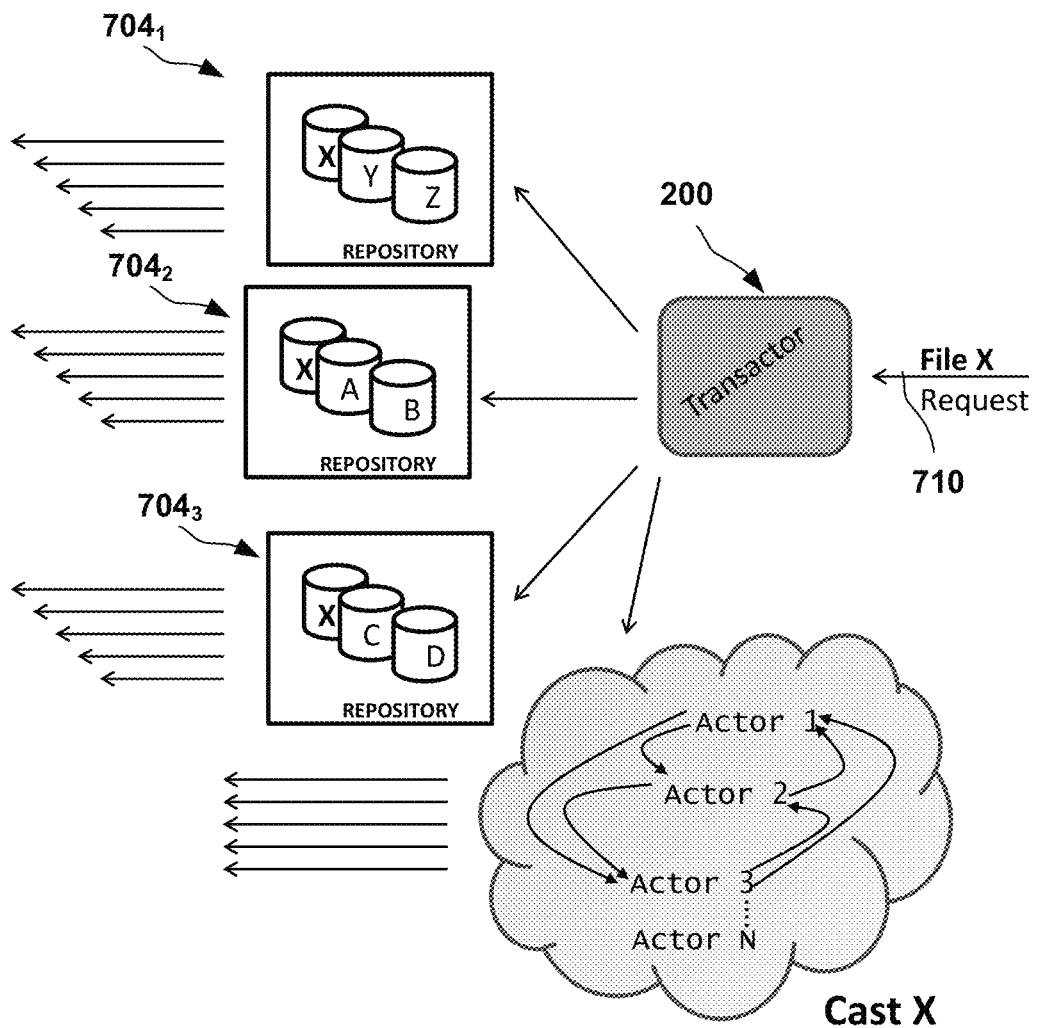

Turning to FIG. 7, it should be appreciated that file X could consist of a file stored in repositories 704 at multiple locations at the time a request 710 is made to download this file on the network. The GeneTorrent™ system can achieve multiple instances of the same file because of the key distribution used to certify copies of file X that it is from one original file. In exemplary embodiments a GeneTorrent™ system can be configured to generate multiple instances of secure parallelized streams from a certified copy of file X from one or more actors to one or more other actors.

In certain embodiments the line of authentication maintained by the Transactor 200 can be to an original copy. In this embodiment the Transactor 200 adds the data certification on top of a "SmartTracker" component that tracks not only who have which file but also tracks biological and clinical knowledge about the files.

For example, using existing protocols it may not be possible to track a specific BAM file and which actors have it or are in the process of obtaining it. However, the SmartTracker may track file specific information contained in these sequence data files on variants, gene expression, copy number variations as well as any disease that might be associated.

In addition, clinical and phenotypic information may be tracked and can be associated with the genome and transcriptome data. In one embodiment the Transactor uses the SmartTracker, conditional access control and a robust encrypt key distribution to assign high affinity actors to a cast based on file X request and essentially on any field of information contained in the sequence data file.

For example, in addition to the Transactor assigning actors to a cast because they are all interested in a particular file X, the actors might be clustered based on information about the file. For example, if the file X is the genome sequence for an individual with disease Y and if it is known that mutations in certain genes on chromosome 17 are associated with the disease, then the Transactor may be more effective in building out a well-defined affinity cast in the early stages of an impending transmission request load to limit any bottleneck.

Bi-Directional Authentication

Embodiments of the GeneTorrent™ protocol disclosed herein provide security for biological sequence data in transit by, for example, running a well-established protocol over Secure Socket Layer (SSL) connections between trusted GeneTorrent™ actors involved in the transfer of file pieces over a network. In one embodiment, the SSL connections will be bi-directionally authenticated in the manner described below.

Figure 8A:
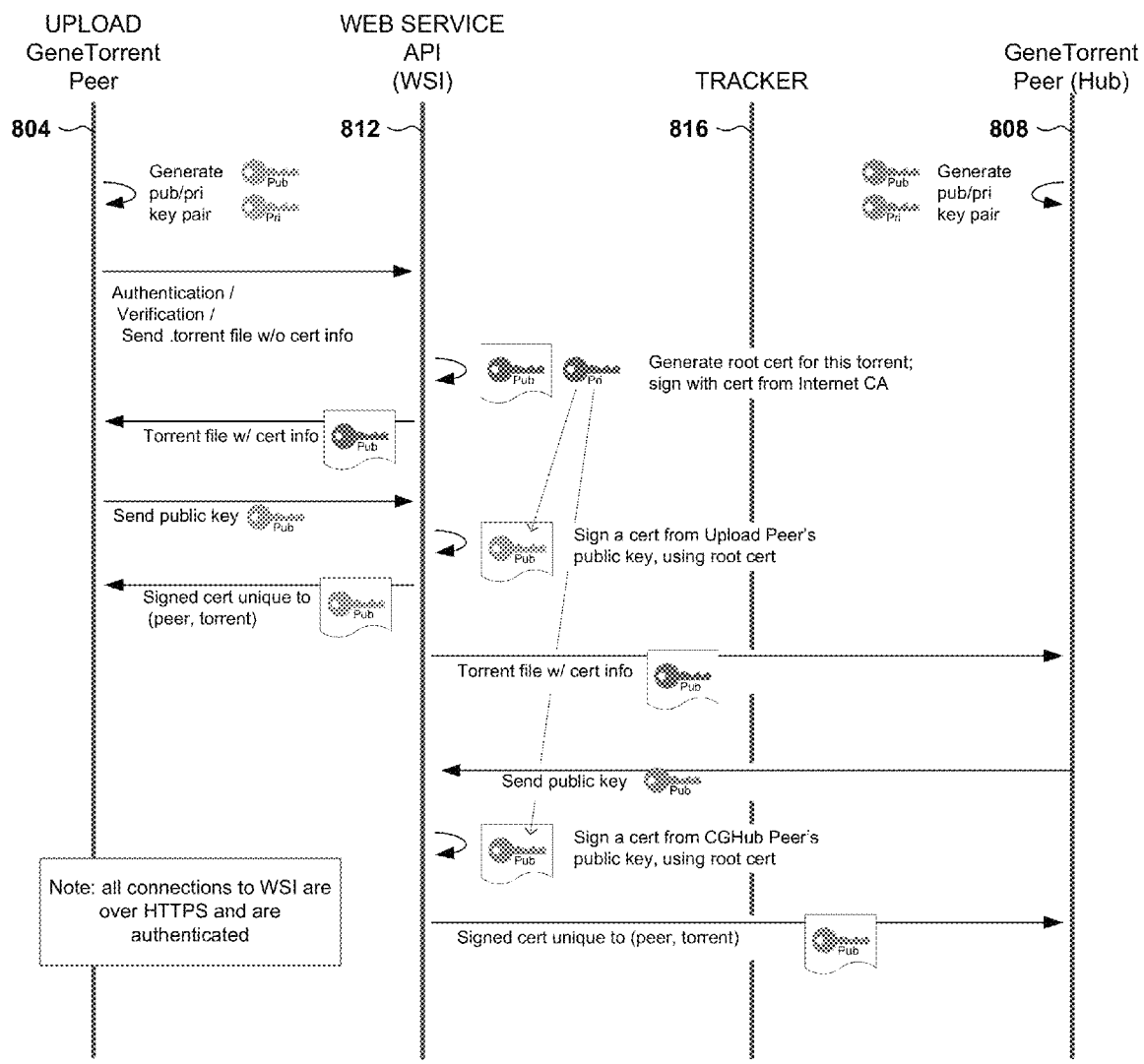
FIGS. 8A-8B illustrate an exemplary sequence of communications occurring between GeneTorrent™ peers executing on a source system(s) and a Genome Data Repository in connection with a file upload operation.
Figure 8B:
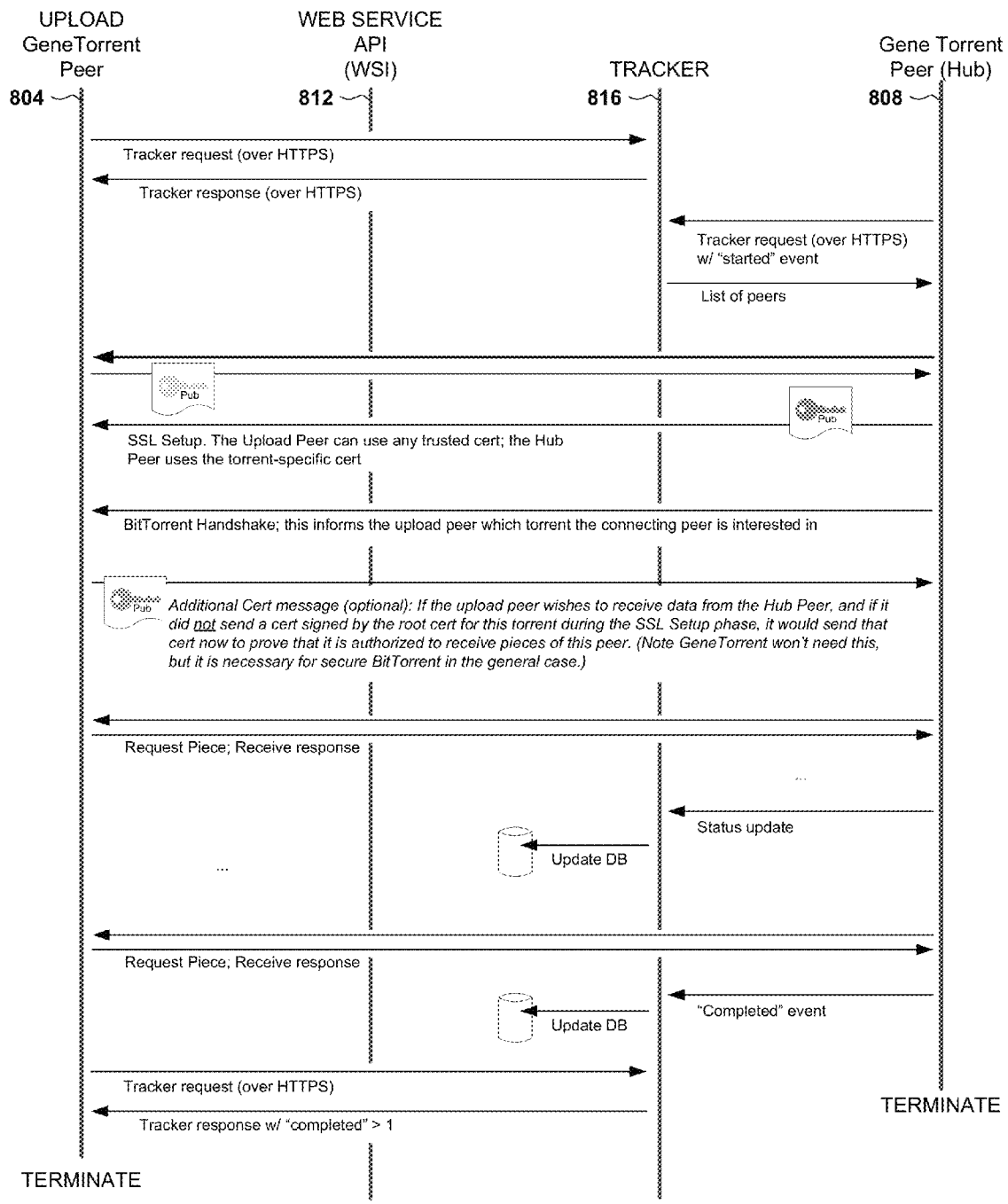

Referring to FIGS. 8A-8B, in a file upload case the GeneTorrent™ client software runs on both a source system(s) 804 and a Hub 808 (e.g., a GDR). In one embodiment the web service interface (WSI) 812 and Tracker 816 run only on the repository systems and mediate the file transfers. As is illustrated by FIG. 8A, in a first stage an exchange of digitally signed certificates takes place.

Certificate Generation

At this point, the uploading source and the GDR have mutually authenticated by exchanging digitally signed certificates that can be traced to a trusted $3^{rd}$ party, i.e., an Internet CA. The certificates are specific to this Gene Torrent Object file and the file it represents, is immune to a replay attack, and is not subject to man-in-the-middle interception.

SSL Session Negotiation

In order to provide enhanced security for the sensitive data on this network, the SSL connections will use the AES-128 cipher, which is a more robust (and FIPS-compliant) cipher than the RC4 cipher typically used.

Parallel Piece Transfers

The typical protocol file transfer takes place, with multiple actors on the side of a repository (e.g., a Genome Data Repository) requesting pieces from an uploader at a source system (e.g., a Genome Sequence Centers (GSC)), until all pieces have been successfully received on the shared file system of the repository.

Session Termination

In one embodiment the SSL session(s) are torn down and the one-time-use Gene Torrent Object file is allowed to expire. The encryption keys that are used to access the data are no longer functional for additional access sessions to this data.

GeneTorrent™ SSL Implementation for File Download

Figure 9A:
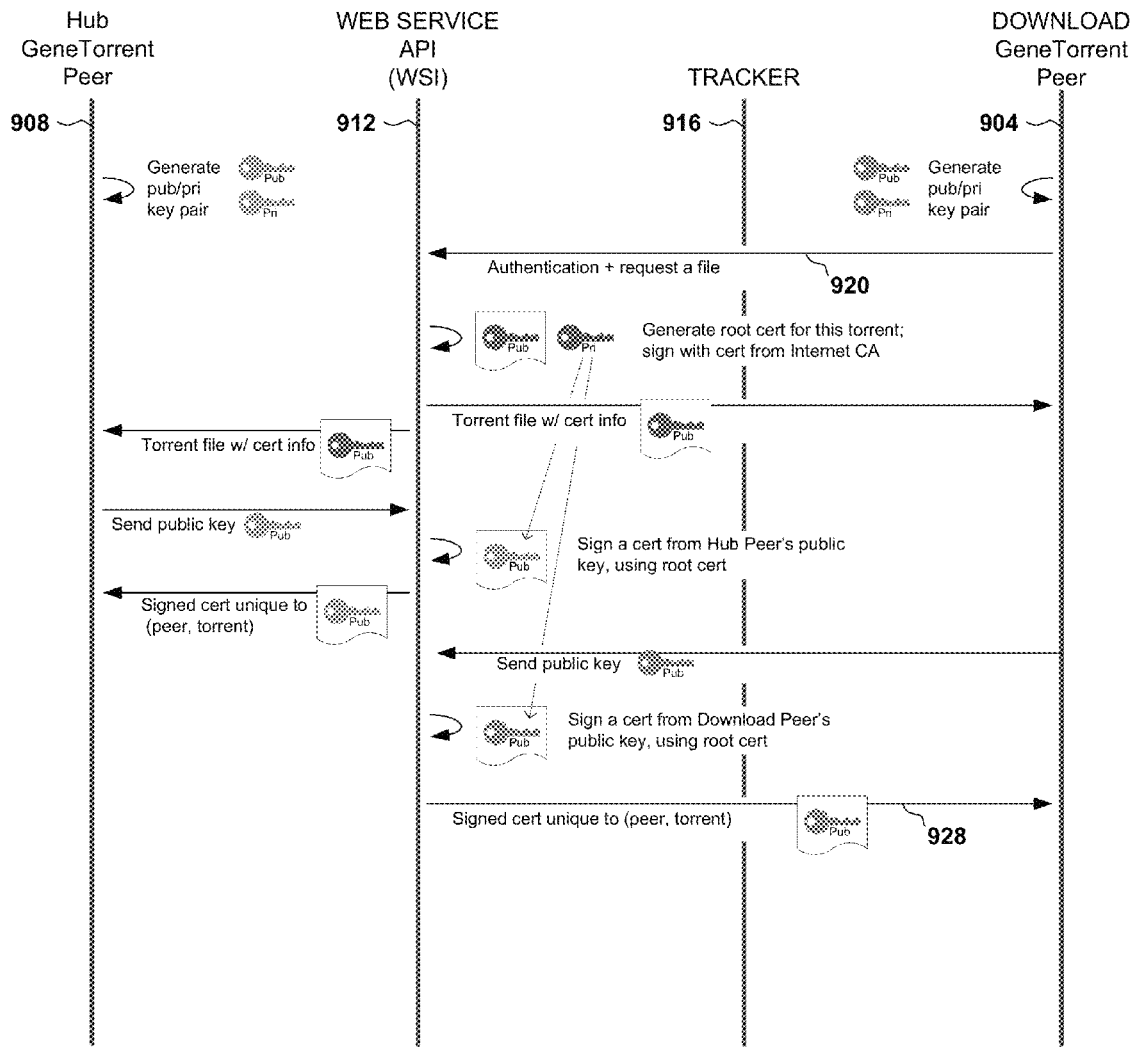
FIGS. 9A-9B provide an illustration of a secure GeneTorrent™ download workflow between client-side GeneTorrent™ data consumers and server-side GeneTorrent™ components.
Figure 9B:
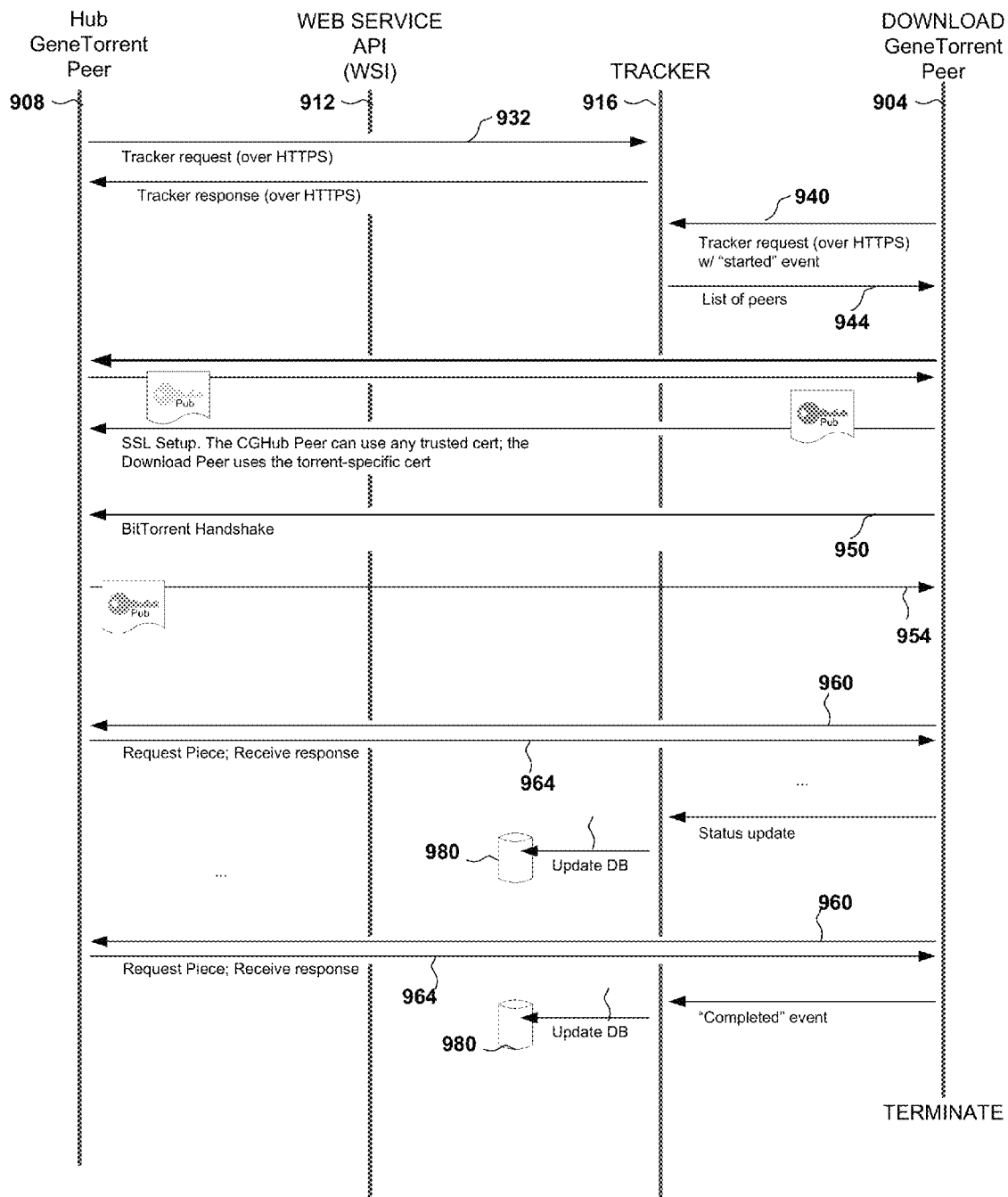

FIGS. 9A-9B provide an illustration of a workflow for a secure GeneTorrent™ file download process between client-side GeneTorrent™ download peers 904 (i.e., data consumers) and the server-side components. In the embodiment of FIGS. 9A-9B these server-side components include a Web services API (WSI) 912 at a Hub 908 (e.g., a GDR), and a Tracker 916.

As shown in FIG. 9A, the workflow is initiated upon a data consumer 904 sending an authentication message and a request for a file to the WSI 912 (stage 920). This initiates the authentication process depicted in FIG. 9A, which culminates in a signed certificate unique to a particular peer and torrent being sent by the WSI 912 to the GeneTorrent™ peer 904 (stage 928).

As shown in FIG. 9B, the GDR 908 continues the download workflow by sending a Tracker request to the Tracker 916 (stage 932). The GeneTorrent™ download peer 904 also sends a Tracker request with a "started" event to the Tracker 916 (stage 940). In response, the Tracker 916 returns a list of peers to the requesting GeneTorrent™ download peer (stage 944). Following performance of an SSL setup procedure involving the GeneTorrent™ download peer 904 and the GDR 908, the download peer 904 initiates a BitTorrent Handshake in order to inform the upload peer, e.g., at the GDR 908, in which torrent the connecting peer may be interested (stage 950). In cases in which the GDR 908 or other upload peer desires to receive data from the download peer 904 and has not sent a certificate signed by the root certificate for the applicable torrent, it sends such a certificate to prove it is authorized (stage 954).

Once the handshaking process has been completed, the download peer 904 requests pieces of the applicable file (stage 960) and receives responses to these requests from the GDR 908 (stage 964). After each piece is received, the download peer 904 provides a status update to the Tracker 916 (stage 970), which then updates its Tracker database 980 (stage 984).

The network flow data that is available on the system can provide powerful statistical correlation data from comparative sequence data analysis. Consider a case where sequence variants data that is transmitted from various GSCs is monitored for quality assurance. In addition, the Tracker 916 may be configured to track pieces of a .gto file to control duplication and distribution of this data.

It is believed that SSL and the necessary certificate management is a novel and key advantage of GeneTorrent™ over public solutions.

GeneTorrent™ Peer Load Balancer

In one embodiment the GeneTorrent™ protocol will be able to scale to accommodate multiple server-side GeneTorrent™ processes, and download requests will be load balanced across processes to optimize server performance. In this embodiment a Load Balancer module will communicate with the WSI 912 over a specified network interface to receive GTO files for each download session. The Load Balancer module will then place the files in the appropriate GeneTorrent™ Peer work queues based on system load and quality of service.

Upon reaching a set threshold level of occurrence of a certain allele this information can be published back to the data consumers as well as all the producers to improve their methods.

Monitoring and Statistics Reporting

Each GDR may maintain a database with full access logs (e.g., which files are uploaded, downloaded and modified by whom) and usage statistics (e.g., average transfer volume and rates, error rates, etc.). In one embodiment these logs will be managed by a Data Manager process using status information obtained from the Tracker database 980. In one embodiment users are permitted to access the data using standard database query and reporting tools.

System Architecture and Principal Components

Figure 10:
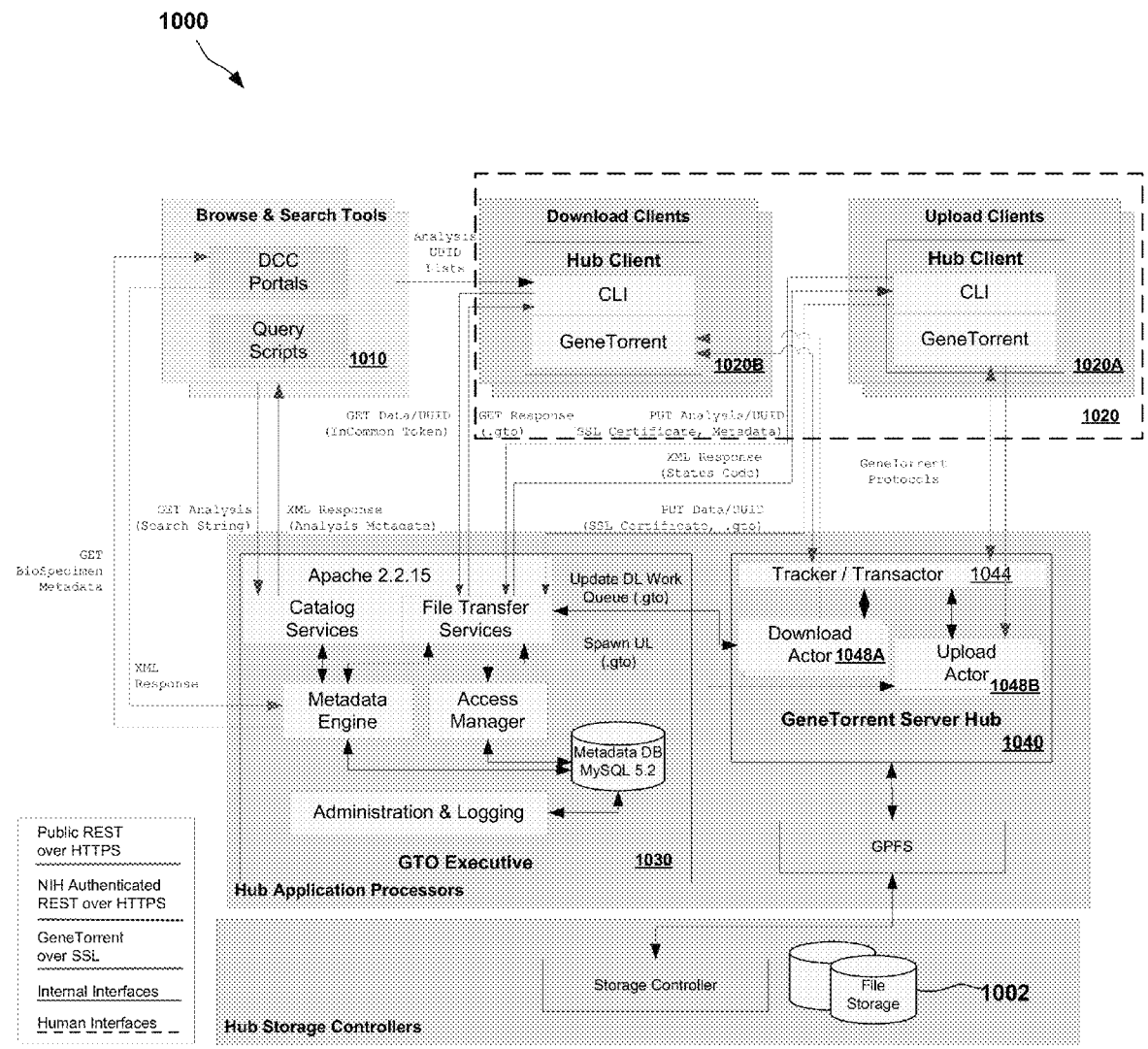
FIG. 10 illustrates an exemplary architecture of a system capable of providing GeneTorrent™ file transfer capability.

Attention is now directed to FIG. 10, which illustrates an exemplary architecture of a system 1000 capable of providing GeneTorrent™ file transfer capability. The system 1000 may operate to transfer files to and from, for example, genome data repositories (GDRs) maintained within storage 1002 or otherwise stored at network locations accessible to the system 1000.

In one embodiment the system 1000 includes the discrete subsystems discussed below, each of which may interface with the others through well-defined, network APIs. In particular, the system 1000 may include a search & browse tools subsystem 1010, a GeneTorrent™ client subsystem 1020, a repository data executive subsystem 1030 and a GeneTorrenf Server Hub subsystem 1040. It should be appreciated that each subsystem can run on the same or different physical servers or other machines.

The search & browse tools subsystem 1010 may include one or more tools (e.g., DCC Data Portal), Web Browser and/or query scripts for enabling users to search file metadata and find objects for download. The GeneTorrent™ client subsystem 1020 provides, among other things, a command line interface (CLI) for secure, high-performance upload and download. File download functionality is provided by GeneTorrent™ download clients 1020A and file upload functionality is provided by GeneTorrent™ upload clients 1020B. The upload and download clients 1020A and 1020B may run on, for example, POSIX workstations with sufficient storage and performance to be installed at sites (GSCs/GDACs) engaged in the generation and processing of genomic information.

The repository data executive subsystem 1030 includes a server Data Manager configured to run on an application processor. The Data Manager is responsible for ensuring the integrity and security of the data and for providing external interfaces for searching, uploading and downloading data. The Data Manager will generally include a SQL database containing metadata corresponding to the sequence data included within files transferred by the system 1000, user information and system monitoring data.

In an exemplary embodiment external interfaces are implemented as RESTful Web Service Interfaces (WSI). In one embodiment the WSI uses Apache and a Solr search index.

In one embodiment the GeneTorrent™ Server Hub subsystem 1040 includes a Tracker/Transactor process 1044 and multiple GeneTorrent™ peer processes 1048 comprised of one or more download actors 1048A and one or more upload actors 1040B. The Tracker/Transactor process 1044 orchestrates the connections and tracks status for transfers between GeneTorrent™ Actors. This process 1044 also clusters individual actors as participants belonging to a cast of actors in a particular affinity group that are all requesting file X. In one embodiment the Tracker/Transactor process 1044 also determines an actor's cast by the file request, the location of the file (with which actor(s)) and the particular actor's credentials to access the file. The Tracker/Transactor process 1044 may also determine the authentication and entitlement of each actor based on authorization rules and using a secure key distribution scheme.

The repository data executive subsystem 1030 and the GeneTorrent™ Server Hub subsystem 1040 may be collectively referred to herein as the "GT Executive" or the "GT Exec".

In one embodiment users will use a web browser or scripts to query the Web Services interface of the GTO Executive and find the desired objects for download. Users can request downloads for either all the objects within an analysis container or individual files. Because creation of the torrent files requires a non-trivial amount of time to calculate the pieces and checksums, in one embodiment the torrents will be stored in each GDR along with the corresponding data files. This will generally require a separate torrent for each data file.

System Operating Modes

In one embodiment the GeneTorrent™ system 1000 functions in three (3) modes: upload, download, and seeder.

Upload mode is used to upload Gene Torrent Object files to the one or more genome data repositories (GDRs) maintained within storage 1002 or otherwise stored at network locations accessible to the system 1000. Download mode is used to download files from the various GDRs on the network. Seeder mode is a mode used within each GDR to create GeneTorrent™ server instances that seed data to download actors in communication with the system 1000 over one or more networks.

General Options (Available to all Modes):

| | |
|---|---|
| -b<br>--bindIP | Bind IP address (default: All IPs on server) |
| -n<br>--noclean | No clean up. Prevents the application from cleaning up after the transaction completes. |
| -v<br>--verbose | Verbose stdout progress reporting (default: no output for successful processing) |
| -vv<br>--moreVerbose | More Verbose stdout progress reporting (this is 2 v's, not a W) |
| Upload options: | |
| -a <file name><br>--analysisFile | Analysis.xml file name, may include a path |
| -p <path><br>--path | Full path to the data files in the analysis file (default: current directory) |
| -s <int value><br>--size | Piece size to use when building the gto file (default: 1048576). If not specified, value auto adjusts based on the size of the data file. |
| -t <url><br>--trackerURL | Tracker URL (this will be made a default once the CGHub Tracker URL is identified) |
| Seeder options: | |
| -c<br>--seeder | Indicates CGHub seeder mode |
| -q <path><br>--queuePath | Queue directory (file system path) to monitor for new .gto files to seed |
| Download options: | |
| -d <VARIABLE><br>--download | Indicates download mode, where VARIABLE is a .gto file, a URI, or an XML file containing a list of URIs. Note that this option may appear multiple times on the command line. |
| -p <path><br>--path | Path to save data files in the gto file(s) (default: Current directory). UUID is part of the gto and will always be added to <path>, so data files will be found at <path>/<UUID>. |
| -z <credential file><br>--password | Full or relative file name of a file containing the security token for this download (default: ~/.gtUserPass) |

Alternate Operational Control Modes

Although in one embodiment the GeneTorrent™ system may be controlled via a command-line in the manner discussed above, in other embodiments the GeneTorrent™ system may be indirectly controlled by a third party application and/or service. This form of interaction may be characterized as a form of "remote control" in that an entity external to the GeneTorrent™ system directs control of upload and download transfers. The external entity may reside on the same machine(s) as the GeneTorrent™ system components or it may reside in an entirely different network, operating in a command and control fashion from afar.

Additionally, in yet others embodiments of the GeneTorrent™ system may utilize automated batching techniques. In particular, in such embodiments the GeneTorrent™ system may be provided with a list of transfers to perform. This list of commands could be issued either all at once or sequentially by another sub-system and/or component without user interaction.

File Security—Layers of Encryption

The GeneTorrent™ system will generally be capable of ingesting files of any format containing genome and transcriptome sequence data and any additional metadata files that are associated. These files are validated, encoded and encrypted in order to maximize transmission rate.

In one aspect the GeneTorrent™ method may be applied to transfer very large files of biological sequence data along with files containing other data and information having a very specific relationship. It is this information in these files that are encrypted and configured in layers associated with a layered data model.

For example, all of the data that is associated with a whole genome or whole exome sequence data could be encrypted within the same layer with one or more keys. This information may include, without limitation, annotation data concerning functional regions of the genome, genes, promoters, repeat sequences, DNA methylations, SNPs, CNVs, structural variants including chromosomal rearrangements.

A second layer of data would include gene expression data including data from splicing, RNA processing, mRNA-Seq and miRNA-Seq data. Another layer of encrypted data associated with the sequence files may include protein function assay results or protein level measurements. Other layers of encryption may include clinical test results and information on drug metabolism and response.

Yet still other layers of encrypted data might include metadata from various procedures from the extraction of the tissue or cell sample to the analyte preparation methods to the conditions of sequencing to the algorithms used for analysis of the sequence and any molecular pathways, drugs and specific disease associations.

For example, the information that is present in the various layers might be made accessible to based on the consent of the owner and also based on the relevance of the information to the user that is making the request.

Consider the case where the user of the data is a genome data analysis center (GDAC) making a request to use the whole genome sequence data to do an in silico screen for colorectal cancer. The owner of the data or an agent will receive a prompt for consent to use the data and user may then be authorized to access those regions of the genome with association to the specific disease based on layered encryption.

The system is designed to track and coordinate all the data contained within these ancillary files. As a result, each of the various genome data repositories and user/analysis systems in communication over a network may have awareness of the location of data as well as the compute clusters and algorithms that are available. In essence, the encrypted layered data is a component part of how this genomic data network comprised of both genome data repositories and user/analysis systems provides content awareness.

As indicated in Table I, in one embodiment the genome data network is configured in such a manner that authorized users are able to access the various layers of encryption with a consent-based conditional access system.

TABLE I

| Layers  | Data Type       | Access Level      |
|---------|-----------------|-------------------|
| Layer 0 | Sequence Files  | General           |
| Layer 1 | variants        | Restricted        |
| Layer 2 | Gene Expression | Restricted        |
| Layer 3 | Pathways/Drugs  | Highly restricted |
| Layer 4 | Disease/disorder| Extreme           |
| Layer 5 | Personal data   |                   |

In this embodiment access rights to the data are stored at the repository and controlled by the rules or operating system applicable to the genome data network (which may be referred to herein as the "network operating system"). The determination with regard to access rights is made by the owner or custodian of the data by giving a one-time static consent or doing it dynamically with a different key per request. This will enable distributed, consent-based access to personal health data in a manner consistent with applicable regulations and laws (e.g., HIPAA).

In one embodiment all of the information associated with every file stored within the genome data network is searchable on a network-wide basis. As a consequence, a user with the proper authorization would be able to submit a query relating to any type of information from Table 1 and receive a response identifying all the genome sequence data files on the network that are accessible to the user based on the consent given by the respective owners of the data within the queried files. For example, a query can be made with reference to all of the genome and transcriptome data that has been uploaded to the genome data network during a predetermined period (e.g., within the last 60 days).

In this case, the response to the query could come from multiple genome data local area networks (gLANs) included within the genome data network. The network operating system may be configured to monitor the consent for access to data and user authorization and be able to effectively authenticate users.

Figure 11:
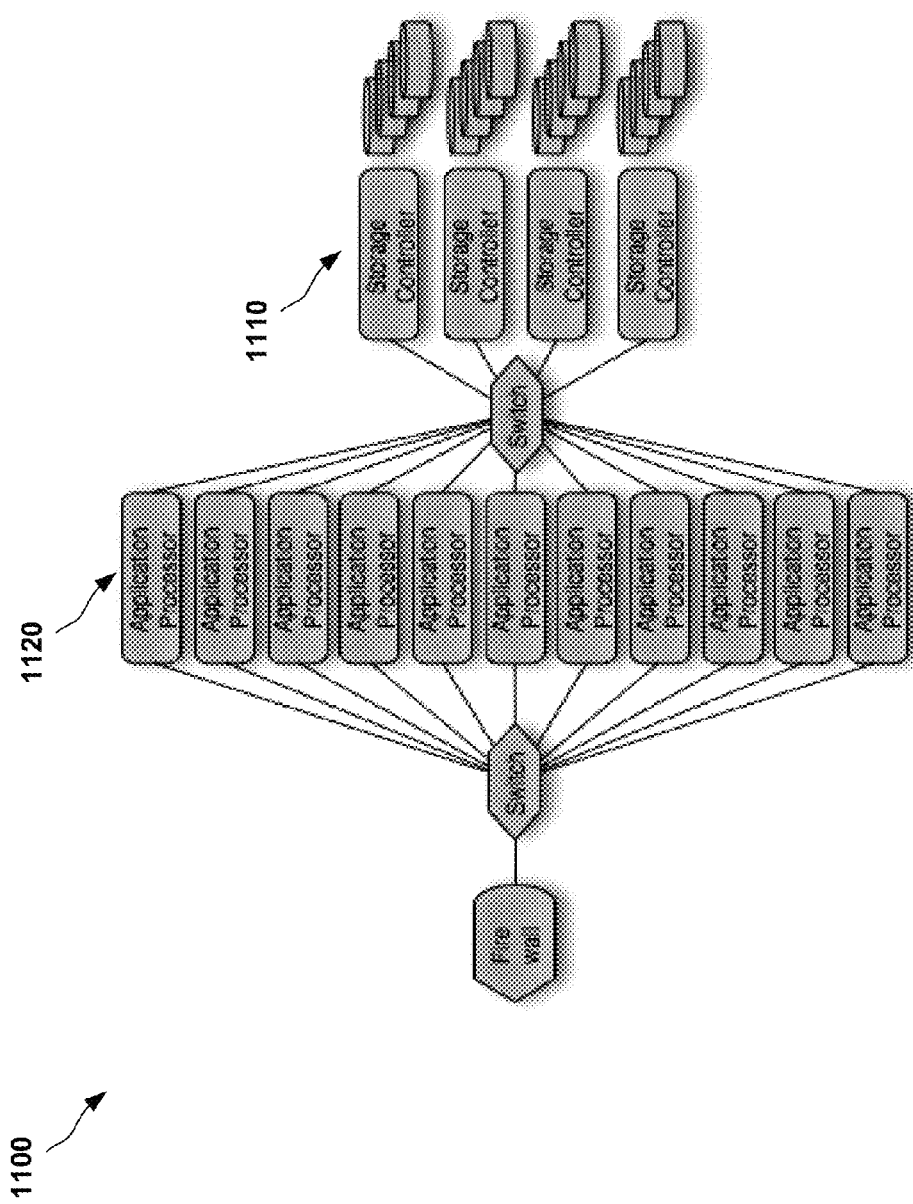
FIG. 11 illustrates a data repository comprising high-speed fiber optic storage and computing infrastructure capable of facilitating the acquisition, secure storage, searching, and secure sharing of genome sequence data and phenotype metadata.

Attention is now directed to FIG. 11, which provides a block diagrammatic representation of an exemplary genome data repository 1100 capable of being used to store genomic and other data accessible to users of a genome data network. The repository 1100 may include high-speed fiber optic storage and computing infrastructure capable of facilitating the acquisition, secure storage, searching, and secure sharing of genome sequence data and phenotype metadata with authorized to access. In one embodiment the repository 1100 provides secure transfer and storage of genome and phenotype information by authorized users and supports multiple simultaneous high capacity transfers across multiple 10 gigabit/second links.

As shown, the repository 1100 includes a plurality of storage controllers 1110 that may be configured to storage relatively large amounts of genomic data. For example, the storage controllers 1110 may be designed to initially store at least 500 Terabytes of genome data (scalable to 5 Petabytes of genome data and architected for 20 Petabytes of genome data). The repository also includes a cluster of application processors 1120 that provide high performance file transfer, security access control, fault protection and workflow monitoring.

Transfer and Ingestion Software

Sequence Producing Centers are anticipated to be a primary source of sequence data. At such Centers, digital representations of biological samples are generated by processing such samples. Optionally, research centers may also upload genome data. In addition, phenotype information and high-level features derived from the raw sequence, the metadata, is produced at the DCC and other sources. In one embodiment software and associated hardware will be located at these centers to perform a genome sequence transfer and ingestion processes. Such software will generally be capable of checking data format and validity prior to initiating uploading to a genome data repository. The software will also preferably perform transfer of genome and metadata information to the data repository and support high capacity transfers at very high data rates (e.g., 10 Gigabits/second).

Genome and Phenotype File Type, Sizes, and Organization

In one embodiment data may be organized and grouped within the data repositories included within a genome data network as follows:

cancer type (lung, ovarian, etc), about 25 types batch (tumor/normal pairs are done in batches of about 100 cases, 5 batches per cancer type)

case/sample ID within the batch (e.g. ID=TCGA-06-145)

The case/sample ID will have various extensions for the various types of files made for each case:

tumor whole genome sequence file (250 GB), tumor exome sequencing file (25 GB), tumor RNA-seq file (<120 GB), tumor miRNA-Seq files tumor CNV files tumor methylation file (<1 GB), blood normal whole genome file (250 Gb), blood normal exome file (25 Gb), blood normal RNA-seq file (<120 GB), blood normal miRNA-Seq files blood normal CNV files blood normal methylation file (<1 GB), adjacenct normal whole genome file (250 GB) and adjacenct normal exome file (25 GB)

Digital Data Repository Configuration

Figure 12:
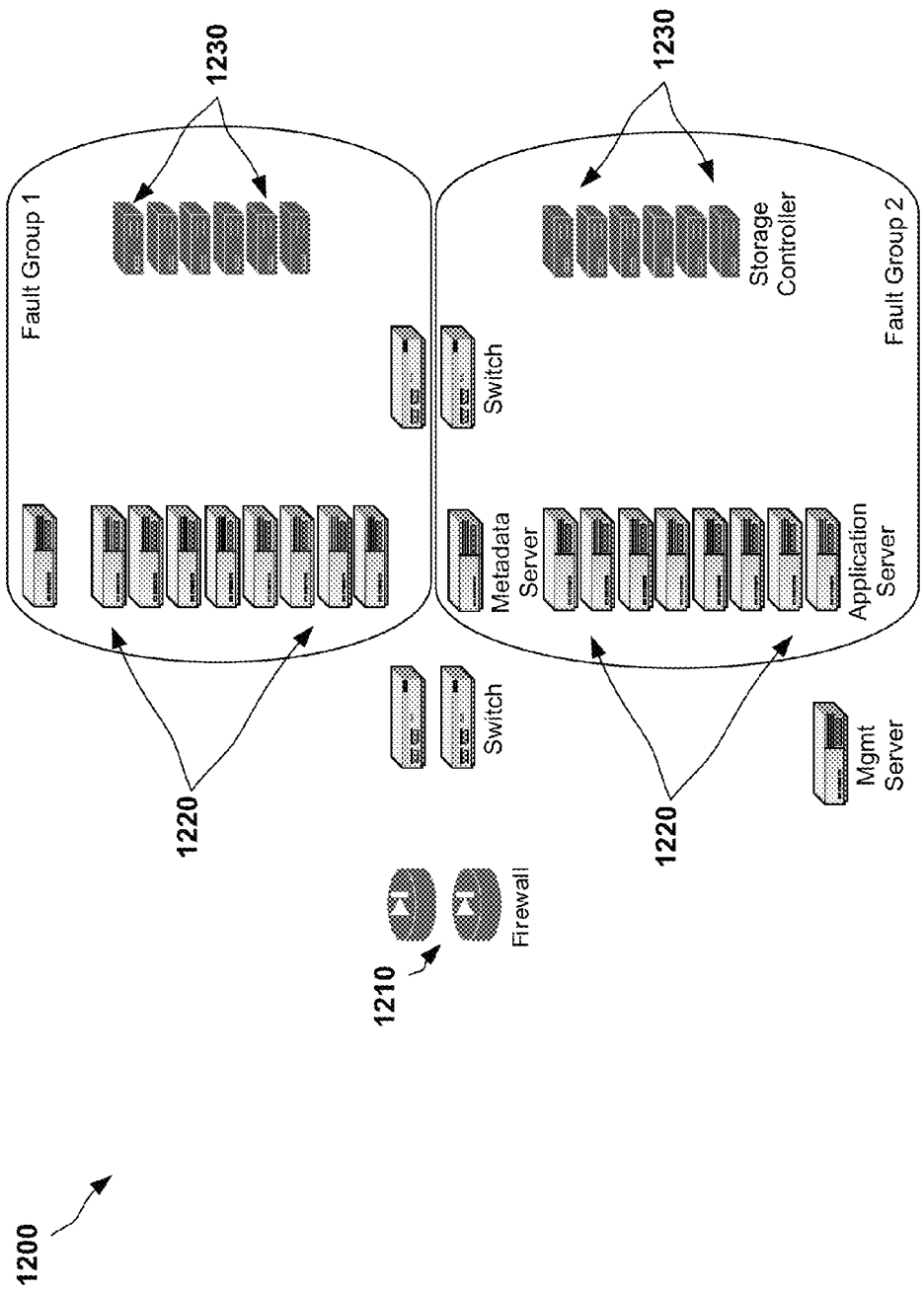
FIG. 12 depicts an implementation of data repository equipment comprised of several levels including a firewall level, application array level, and storage array level.

Referring to FIG. 12, in one embodiment the equipment used to implement an exemplary digital data repository 1200, such as a genome data repository, may be grouped within three main levels: (1) firewall 1210, (2) application array 1220, and (3) storage array 1230. A 10 Gbps Ethernet Switch may be used to interconnect the equipment. Separate VLANs and layer 3 filters may be used to logically separate the levels of the system to maximize performance and prevent unauthorized access.

In one embodiment the firewalls provide Layer 4 protection for the datacenter from the external network. The application array provides the primary logic for user access to the storage, including access control, catalog perusal, and file transfer. The storage array provides scalable, high performance, reliable access to high capacity disks. All levels may be connected over LOGE networks, separated into two networks partitioned for storage and application. The system is also partitioned into two separate fault groups wherein a storage failure can be isolated.

Figure 13:
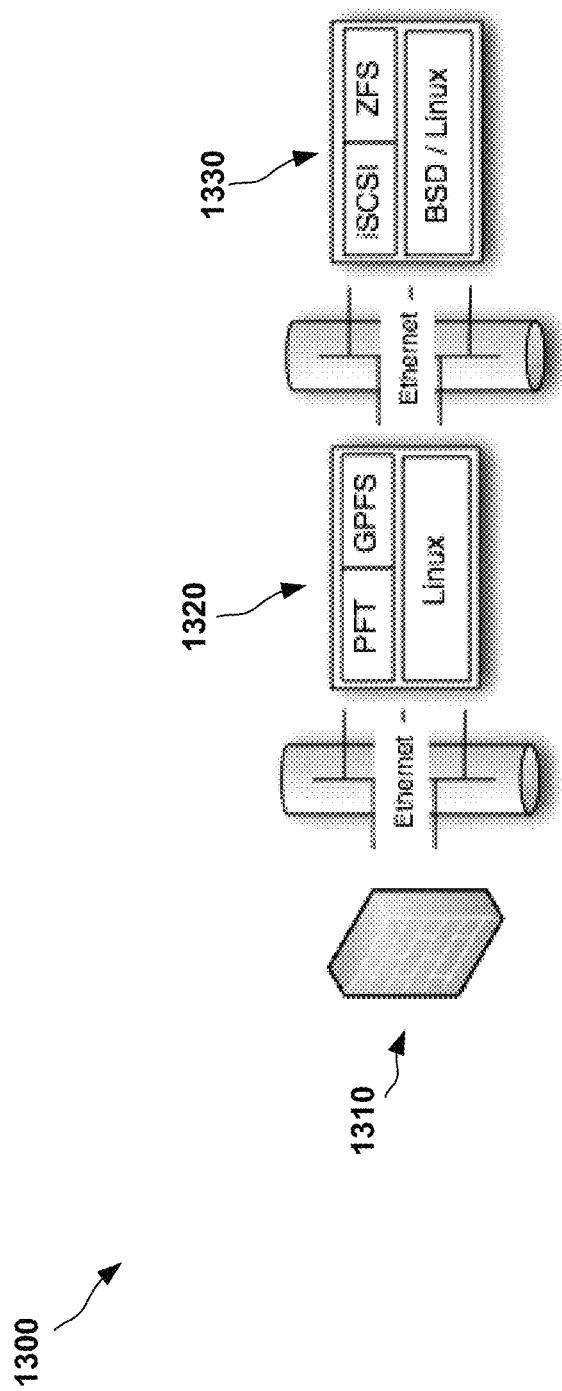
FIG. 13 illustrates an exemplary software configuration associated with the multi-level data repository of FIG. 12.

Referring to FIG. 13, in one embodiment the software configuration of the levels of the exemplary digital data repository 1300 consist of the following:

1) Firewall 1310—dedicated appliance or Linux based firewall such as Vyatta.

2) Application Server 1320—Linux Operating System, GPFS, parallel file transfer (PFT) application, Apache, node.js. Additional servers are dedicated for file system metadata and cluster management.

3) Storage Controller 1330—BSD or Linux, ZFS exporting iSCSI volumes.

In one embodiment software at sequence producing centers (e.g., at genome sequencing centers (GSCs)) will ensure that files are properly formed and content meets acceptable criteria before upload operation can commence. This ensures that data reaching the applicable digital data repository will be usable and reduces the troubleshooting time in identifying and correcting incorrect data.

Cloud-Related Applications

A number of organizations have developed "cloud-based" services to enable enterprise and other organizations to manage data and applications within a network-based, i.e., "cloud" environment. For example, Microsoft's Windows Azure offers multiple services to assist customers in managing their data in the cloud. In particular, the SQL Database service offering enables entities to quickly develop and manage applications in the cloud.

However, one impediment to utilization of such cloud-based services by, for example, enterprise organizations is the difficulty in transferring large data files between an enterprise's data center and the cloud. As mentioned above, the additive increase/multiplicative decrease algorithm used by TCP to avoid congestion and control bandwidth usage can impede the transmission rate of very large sequence data files, even on high-speed networks. For at least this reason conventional protocols for transferring bulk data (e.g., data files) tend to experience potentially severe performance degradation over available Internet connections. When TCP-based or other conventional techniques are used, such transfer to and from the cloud is often characterized by slow speed, high failure rates, and high risk of data corruption. Transfer of large amounts of data often occurs when, for example, an enterprise initiates a very large initial upload of data from a data center to a cloud service provider, a periodic back up is commenced, or when multiple sources of data are consolidated and made available through the cloud.

Figure 14:
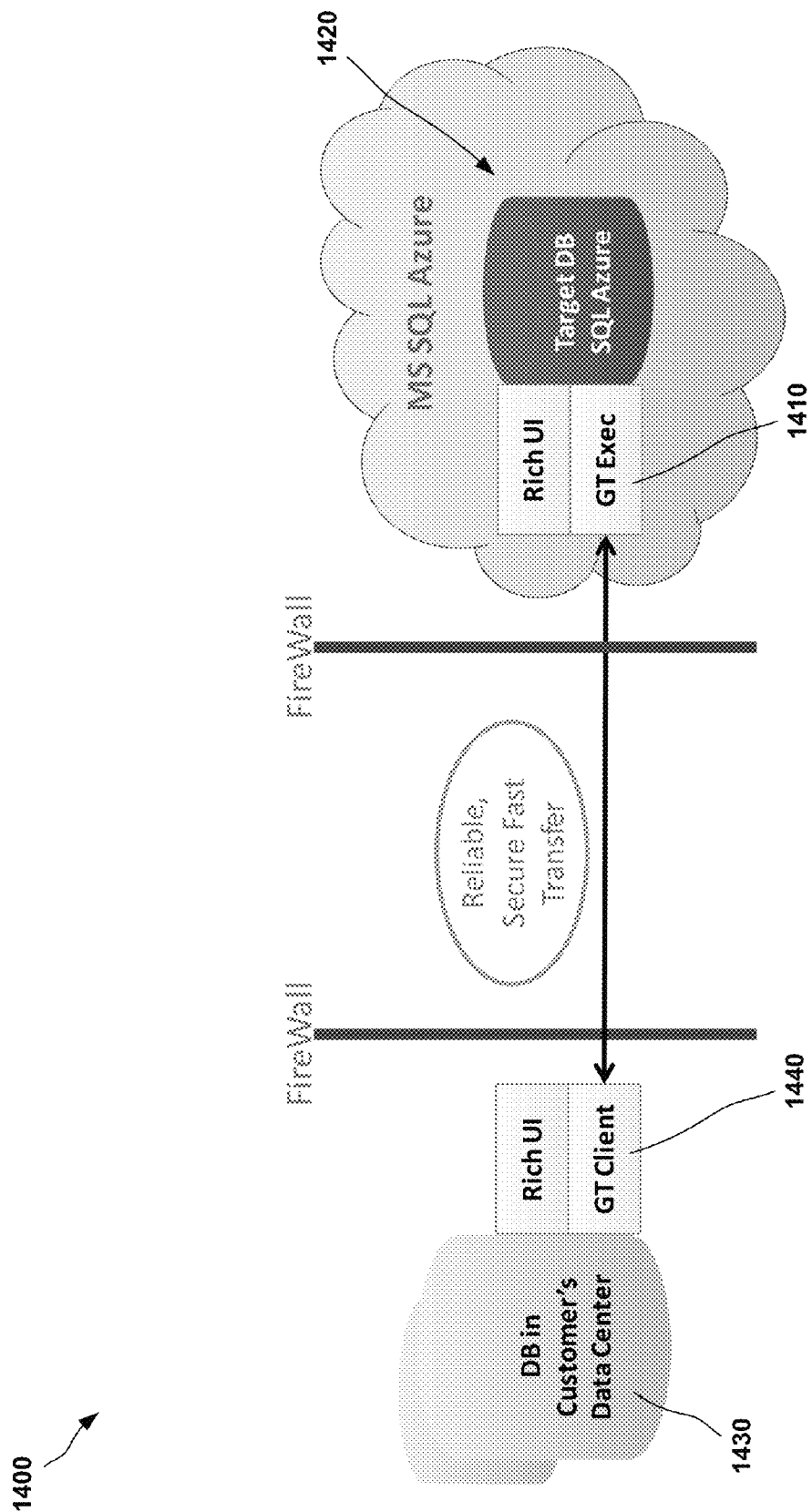
FIG. 14 illustrates an implementation of an GeneTorrent™ file transfer system within a cloud-based environment.

Attention is now directed to FIG. 14, which illustrates an implementation of the GeneTorrent™ system 1400 within a cloud-based environment. As shown, a GT Executive 1410 ("GT Exec") runs within an instantiation of a cloud-based database 1420 (e.g., a Windows Azure database) and functions as a "file server". In particular, the GT Exec 1410 may handle authentication and authorization and be designed to function as a federated single sign-on system. A metadata catalog within the GT Exec may be customized and managed.

The GeneTorrent™ system enables a cloud-based database or other cloud-based platform to faciliate offering high-speed transfer of large data files as a service. For example, the GT Exec may provide a customized portal for each customer or other user to receive requests for data transfers from a particular data center 1430 to a cloud-based database, or vice-versa. In one embodiment the GT Exec would cooperate with a GT client 1440 within each data center to facilitate transfers of large data files to and from the cloud-based database.

Figure 15:
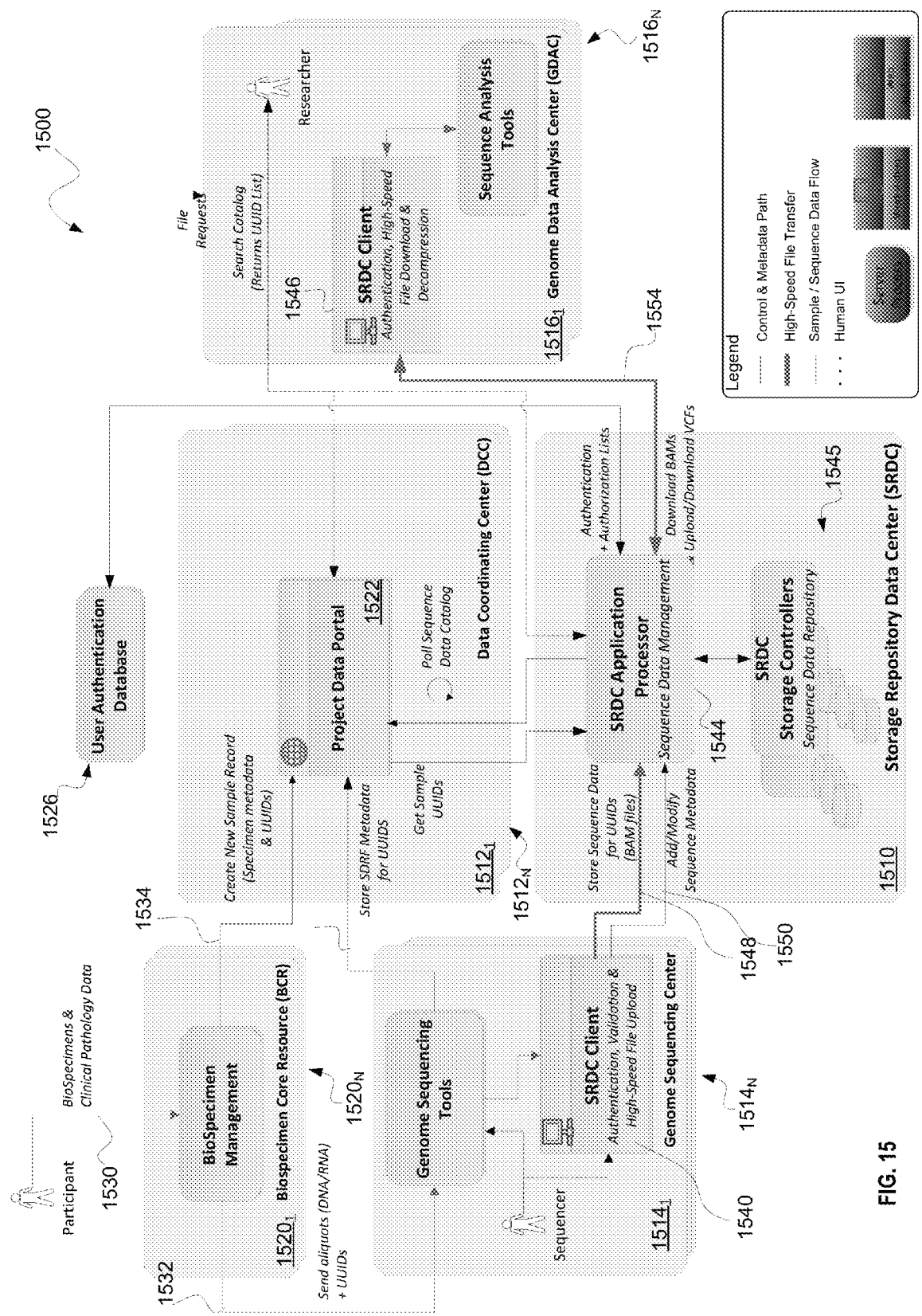
FIG. 15 illustratively represents a genome sequence data system incorporating a high capacity, high throughput networked storage data center (SRDC) configured to utilize the GeneTorrent™ file transfer protocol.

Exemplary Conditional Access System Facilitating Querying and High-Speed Distribution of Genomic Sequence Information System Overview and Workflow Attention is now directed to FIG. 15, which illustratively represents a genome sequence data system 1500 incorporating a high capacity, high throughput networked storage data center (SRDC) 1510 configured to utilize the GeneTorrent™ file transfer protocol described herein. The SRDC 1510, which contains genomic sequence data and related information, is in network communication with one or more DCCs 1512, one or more GSCs 1514 and one or more GDACs 1516. In an exemplary embodiment such network communication is designed to take place over one or more existing wide area networks, such as the Internet. The SRDC 1510 may function as a central repository for the GSCs 1514 to store, and GDACs 1516 to retrieve, sequence data and associated metadata.

As is discussed below, a typical workflow scenario involving the system 1500 may begin with submission of a tissue sample to a BCR 1520 for preparation of genome analyte. The workflow continues with DNA/RNA sequencing and characterization by a GSC 1514, upload of the resultant sequence data and related information to the SRDC 1510, and finally download to researchers at a GDAC 1516 for data analysis. The SRDC 1510 also synchronizes with the DCC 1512 or equivalent system configured to provide the primary coordination portal for researchers or other personnel involved with a particular research initiative or other project. In general, the applicable DCC 1512 maintains the higher-level study attributes and clinical data associated with each tissue sample. The SRDC 1510 will query the applicable DCC 1512 to verify that submitted data is associated with a valid sample. The DCCs 1512 can also retrieve catalog information from an external source and allow users to perform queries across project, sample and sequence data.

Considering now the workflow of FIG. 15 in greater detail, a bio-specimen (e.g., a tissue sample) is furnished to a BCR 1520 and used as the basis for preparation of a genome analyte. Aliquots of the analyte (e.g., DNA or RNA) are then shipped to a GSC 1514 for sequencing and characterization. The GSC 1514 uploads the resultant sequence data and associated metadata to the SRDC 1510 and may transfer other metadata, e.g., Sample and Data Relationship Format (SDRF) metadata, to a project data portal 1522 provided by the DCC 1512. Once stored within the SRDC 1510, the sequence data and associated data may be queried and downloaded by authorized personnel (e.g., researchers) associated with the GDACs 1516.

During operation of the system 1510, the SRDC 1510 will generally synchronize information, and otherwise coordinate closely, with the DCCs 1512 respectively providing coordination portals for various projects or groups of researchers. In an exemplary embodiment each of the DCCs 1512 maintains the higher-level study attributes associated with at least one such project as well as clinical data associated with each sample. The SRDC 1510 will query the appropriate DCC 1512 to verify that data submitted by a GSC 1514 is associated with a valid sample. In certain embodiments some or all of the DCCs 1512 may retrieve catalog information in order to enable users at the GDACs

1516 to perform queries across project, sample and sequence data. In other embodiments queries from GDACs 1516 will be received through a portal or other interface established by the repository 1510. In one embodiment the repository 1510 consults an external user authentication database 1526 in connection with authorization of users for uploading, downloading, and/or querying of sequence information. As is discussed below, users may be authorized for different roles with respect to different projects coordinated by the DCCs 1512.

As shown in FIG. 15, in a stage 1530 tissue samples and any related clinical pathology data are submitted to one of the BCRs by, for example, a tissue source site (not shown). The BCR 1520 prepares the samples for a particular GSC 1514 and assigns a unique ID ("UUID") to each aliquot. Once prepared, the BCR 1520 sends the physical aliquot samples and anonymized metadata containing the UUID of the aliquot to the GSC 1514 (stage 1532). The BCR 1520 also generally electronically transmits the metadata associated with the samples to the DCC 1512 (stage 1534) corresponding to the project associated with the submitted tissue sample. Such metadata may include, for example, information identifying the tissue source site, sample type, analyte type, patient ID, and other information characterizing the sample or the facilities/equipment used to obtain the sample. The DCC 1512 then creates a new sample record based upon this metadata, which is associated with the UUID corresponding to the aliquot. This metadata can then be retrieved from the DCC 1512 through, for example, a web interface which may or may not be provided by the project data portal 1522 of the DCC 1512.

The GSC 1514 to which the sample is provided will perform sequencing and thereby generate BAM file(s), or other files of predefined type, containing the resultant sequence information. The GSC 1514 then defines an analysis object ("Analysis object"), which in one embodiment includes a metadata file and the BAM files(s) corresponding to the metadata. The GSC 1514 also assigns a UUID to the Analysis object. An SRDC upload client 1540 at the GSC 1514 then initiates the sequence submission process by passing a user certification/session token and the submission metadata to an SRDC application processor 1544 for validation. If validation is successful, the SRDC application processor 1544 will create a database entry for the Analysis object and each of its constituent BAM files. As is discussed below, the SRDC application processor 1544 will then track the status of the submission as it moves from loading, through any validation or transfer errors, until it is ready for download by a SRDC download client 1546 within a GDAC 1516. As shown, the SRDC application processor 1544 is in communication with a sequence data repository 1545 configured to physically store submissions of sequence data from the GSCs 1514.

Although a primary function of the SRDC download client 1546 will be to download files of sequence data and related metadata from the SRDC 1510, in certain embodiments the SRDC download client 1546 may also be configured to upload sequence-related information (e.g., VCF files resulting from the processing of downloaded sequence data) back to the SRDC 1510.

In one embodiment each metadata file may include references to the UUIDs corresponding to all of the sequence data files (e.g., BAM files or other sequence data files of predefined type) and aliquots linked to the bio-specimen data (i.e., data related to the initial tissue sample) maintained within the DCC 1512. Alternatively, this information may be included within a separate file which is independently provided by the GSC 1514 to the SRDC 1510 as part of the sequence submission process. The SRDC 1510 may then verify that these UUIDs correspond to valid UUIDs stored within the DCC 1512 before creating a corresponding submission record and UUID corresponding to each Analysis object (and potentially each individual BAM file of the Analysis object) to be uploaded. In addition, the sequence data associated with a given submission may be suppressed, and new sequence data can be submitted for the same sample. This may occur with respect to cases in which, for example, it is desired to "top off" a previous submission with more complete coverage.

As is discussed below, in one embodiment the SRDC upload client 1540 may utilize the GeneTorrent™ high-speed, parallelized file transfer process to transfer the BAM file(s) associated with the Analysis object to the SRDC 1510 (stage 1548). The associated metadata, which will generally be included within a file of inconsequential size relative to the size of the Analysis object, may then be separately sent to the SRDC 1510 using a conventional file transfer process (stage 1550). The SRDC download client 1546 may utilize a substantially similar or identical high-speed, parallelized file transfer process to transfer the BAM file(s) stored within the SRDC 1510 to the SRDC upload/download client 1546 (stage 1554).

In one embodiment the repository 1510 maintains a list of "valid" bio-specimens (e.g., tissue samples) for a particular project and regularly synchronizes this list to corresponding information maintained at the corresponding DCC 1512. This enables the sequence information corresponding to a particular sample to be redacted at the SRDC 1510 in response to information received from the DCC 1512. For example, if the owner of a particular tissue sample at some point revokes consent relating to the download of sequence information derived from the sample, such sequence information could be redacted at the SRDC 1510. In certain cases the metadata information associated with such redacted sequence information could be searched in response to queries submitted by GDACs 1516, but the associated, redacted sequence information would not be available for download. In other embodiments only GDAC personnel with a certain authorization or subscription level would be permitted to download sequence information corresponding to metadata identified in response to a query received from a GDAC 1516; that is, such sequence information would be appear to be redacted or otherwise suppressed or unavailable when identified in metadata returned in response to queries received from unauthorized users.

System Architecture

Figure 16:
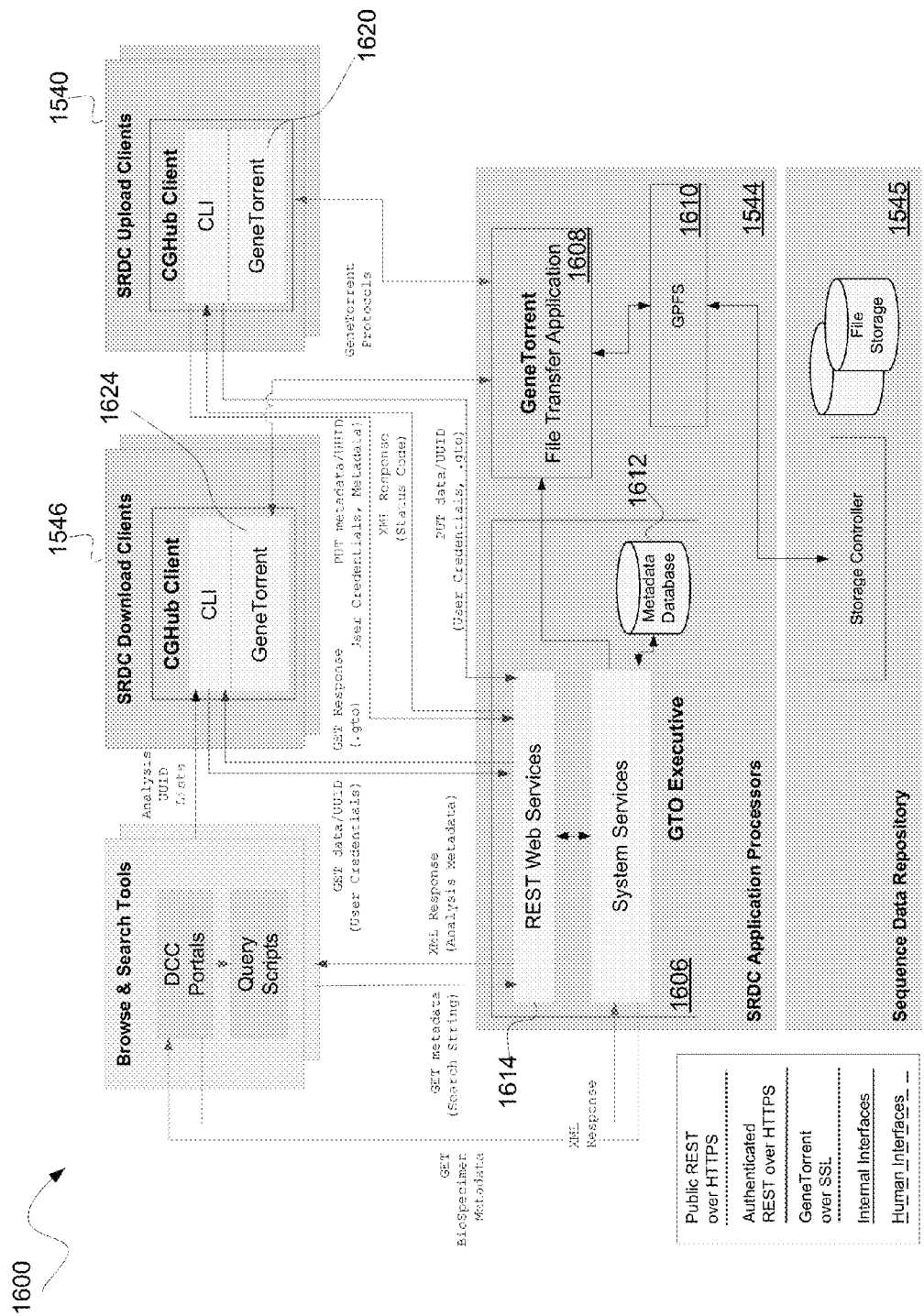
FIG. 16 illustrates an exemplary architecture of an SRDC and SRDC upload/download clients.

Attention is now directed to FIG. 16, which illustrates an exemplary architecture 1600 of the SRDC 1510 and SRDC upload/download clients 1540/1546. As shown, in one embodiment the SRDC application processor 1544 is comprised of a GTO Executive™ subsystem 1606, a GeneTorrent™ parallel file transfer application 1608, and a file system client such as General Parallel File System (GPFS) client 1610. The application processor 1544 is a server configured to host the GPFS client 1610 and applications making use of the sequence data stored within the sequence data repository 1545. In the embodiment of FIG. 16 such applications include, for example, the GeneTorrent™ parallel file transfer application 1608 and the GTO Executive™ subsystem 1606. These applications support, for example, data submissions and catalog queries, high-speed transfer of genomic data files, robust file storage and system administration.

In the embodiment of FIG. 16, the GTO Executive™ subsystem 1606 implements repository data management and security services, includes a metadata database 1612, and provides application programming interfaces (APIs). The GTO Executive™ subsystem 1606 may use the Linux-Apache-MySQL-PHP (LAMP) software stack along with a Solr index to facilitate fast, flexible searching of the metadata database 1612. The GTO Executive™ subsystem 1606 may run on the SRDC application processors 1544. During operation, the GTO Executive™ subsystem 1606 validates and stores analysis object metadata, indexes the sequence data storage, and provides APIs through REST Web Services 1614 to facilitate user queries and client transfer requests. The APIs provided by the REST Web Services 1614 can also be used by party systems including DCCs, or may be used for user scripts and custom tools developed by GSCs 1514 and GDACs 1516.

The file transfer subsystem 1610 implements the GeneTorrent™ protocols that interface with, on the one hand, the SRDC upload clients 1540 and SRDC download clients 1546 and, on the other hand, the GTO Executive™ subsystem 1606 and the sequence data repository 1545.

The metadata database 1612 may comprise, for example, a MySQL database configured to manage a file catalog and the metadata associated with the sequence data stored within the repository 1545. In one embodiment minimal attributes are maintained in the database 1612 to allow for efficient search and retrieval. The database 1612 includes lookup tables capable of being synchronized with the project data portals 1522 so as to facilitate linking of the sequencing data stored in the repository 1545 with project and bio-specimen data. Project specific metadata, access rights and validation rules will be layered on top of a core file management infrastructure. In one embodiment the database 1612 provides a structured representation of the information included within the XML metadata files submitted (during stage 1550) in association with the sequence data stored within the repository 1545.

In other embodiments the GTO Executive™ subsystem 1606 may store such XML metadata files in addition to, or rather than, replicating the information contained within such files within the schema of the metadata database 1612. In such an embodiment users may issue queries relating to common attribute/value pairs as well as with respect to free form strings within the XML data, including user-defined fields. This may facilitate searches directed to attribute/value pairs included within the XML metadata files uploaded during stage 1550 not represented within the schema of the metadata database 1612. In this way an integrated query interface may be maintained across the database 1612 and the XML metadata files without incurring the added expense and complexity of maintaining a database for infrequently used attributes.

As may be appreciated with reference to FIG. 16, the GeneTorrent™ parallel file transfer application 1608 functions in conjunction with a GeneTorrent™ client application 1620 within the SRDC upload client 1540 located at a GSC 1514 and with a GeneTorrent™ client application 1624 within the SRDC download client 1546 located at a GDAC 1516. During operation, each GeneTorrent™ client application 1620, 1624 may be invoked using a command line interface (CLI) for ease of scripting.

File Submission, Transfer and Querying Operations

General Overview

In one embodiment the file submission, download and catalog query interfaces provided by the GTO Executive™ subsystem 1606 of the SRDC 1510 are based on Representational State Transfer ("REST") architectural principles. In this embodiment such interfaces are designed to enable HTTP-based remote procedures for programmatic access; querying using all metadata fields; querying, uploading, and downloading one or more files; each item or "thing" be accorded a unique identifier (UUID); and primarily stateless communication. Adherence to these principles enables the GTO Executive™ subsystem 1606 to implement heterogeneous application-to-application communication simply, easily and quickly using standard protocols such as HTTPS. This facilitates integration between the SRDC 1510 and various upload and download clients and one or more DCCs 1512. The disclosed architecture also facilitates, for example, the use by GSCs 1514 and GDACs 1516 of simple, automated scripts to search the catalog(s) maintained by the SRDC 1510 and/or DCCs 1512 and the checking of object status.

As was indicated above, files submitted for uploading or identified for downloading may be securely transferred to and from the SDRC 1510 in parallel fashion using the GeneTorrent™ parallel file transfer application. In one embodiment this application provides a command-line-driven interface suitable to casual (manual) use as well as programmatic invocation from scripts or other workflow automation.

In upload mode, the GeneTorrent™ application 1608 and a GeneTorrent™ upload client 1620 cooperate to effect submission of a set of one or more sequence data files (e.g., BAM files) to the SDRC 1510. In one embodiment effecting such a submission involves adding the submission to one or more catalogs maintained by SDRC 1510 or DCC 1512, verifying the associated metadata to be uploaded, storing and indexing the metadata for search, storing the sequence data in replicated persistent storage within the sequence data repository 1545, and setting access rules based on, for example, consent agreements associated with the tissue samples from which the sequence data files are derived.

In download mode, the GeneTorrent™ application 1608 and a GeneTorrent™ download client 1624 cooperate to retrieve a bundle of one or more sequence data files from the SDRC 1510. In one embodiment retrieving a sequence data file from the sequence data repository involves 1545 verifying the requesting user is authorized to view the data within the file, storing the sequence data in local persistent storage at, for example, an SDRC download client 1546, and verifying that the transfer was performed correctly.

In both the upload and download modes, the actual transfers of the sequence data files are preferably authenticated (i.e., only users associated with the appropriate permissions relative to the file may access its sequence data) and authorized (i.e., only users authorized in view of project-specific or other rules maintained by the SDRC 1510 and/or DCC 1512 are permitted to download the identified sequence data file). Such transfers are also preferably secured in that the sequence data is strongly encrypted when transiting the network and reliable (i.e., files may be presumed to have been transferred essentially intact and uncorrupted unless the GeneTorrent™ application provides an indication to the contrary).

In one embodiment each GeneTorrent™ client provides a command line interface to the end user. Through this interface one of two operating modes typically may be invoked: upload and download. When operative in upload mode, the GeneTorrent™ client operates in concert with the GeneTorrent™ application 1608 to upload files to the SDRC 1510. When operative in download mode, the GeneTorrent™ client and the GeneTorrent™ application 1608 cooperate to download files to the client from SDRC 1510. In addition, the GTO executive subsystem 1606 may instruct the GeneTorrent™ application 1608 to enter an "actor" mode during which multiple GeneTorrent™ server instances are created for use in performing parallel transfers to/from the sequence data repository 1545.

During operation of the system 1500, the GeneTorrent™ application 1608 executes on one or more SRDC application processors 1544 to manage file transfers to from GeneTorrent™ clients 1620 at GSCs 1514 and to/from GeneTorrent™ clients 1624 at GDACs 1516. In one embodiment multiple GeneTorrent™ server processes executing on the application processors 1544 listen for download requests, and multiple GeneTorrent™ upload actor instances are spawned when an upload request is received from a GSC 1514 (or, in certain cases, from a GDAC 1516). In the present embodiment, application server instances ("AppServer Instances") executing on the application processors 1544 may be configured as either GeneTorrent™ upload actor instances or GeneTorrent™ download actor instances. The allocation of AppServer Instances among GeneTorrent™ upload and download actor instances may be made in accordance with, for example, the number and type of upload and download requests received from peer GeneTorrent™ instances at the GSCs 1514 and GDACs 1516. For example, during periods in which a higher number of download requests are received from GDACs 1516 relative to the number of upload requests from GSCs 1514, more of the AppServer Instances executing on the application processors 1544 may be configured as GeneTorrent™ download actor instances. Conversely, more of the AppServer Instances executing on the application processors 1544 may be configured as GeneTorrent™ upload actor instances during times in which a relatively larger number of upload requests are received. The GTO Executive™ subsystem 1606 dynamically load balances across the application processors 1544 to allocate capacity for multiple upload and download processes, allowing it to better respond to the normal fluctuations in GSC and GDAC workflows. Moreover, performance with respect to a particular GeneTorrent™ upload or download session may be enhanced by allocating a relatively larger number of GeneTorrent™ actor instances to such process.

Figure 17:
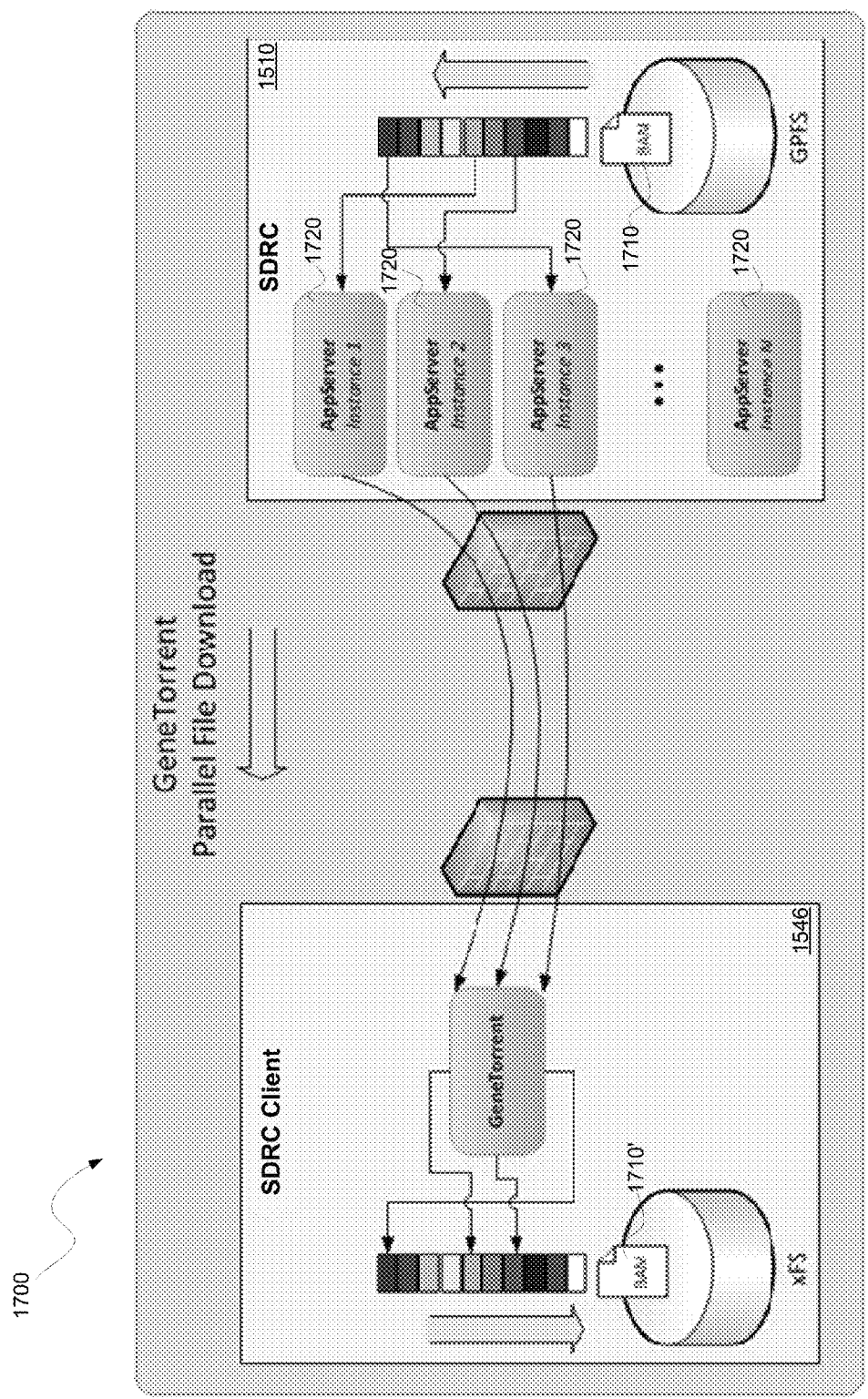
FIG. 17 provides an illustrative representation of an exemplary GeneTorrent™ parallel file transfer process used in connection with the transfer of a sequence data file from the SRDC to a user at a GDAC.

FIG. 17 provides an illustrative representation of an exemplary GeneTorrent™ parallel file transfer process 1700 used in connection with the transfer of a sequence data file 1710 from the SDRC 1510 to a user at a GDAC 1516. As shown in FIG. 17, multiple AppServer instances 1720 are configured as GeneTorrent™ download actor instances to facilitate the transfer of the sequence data file (e.g., a BAM file) to multiple GeneTorrent™ download peer instances (not separately shown) spawned by the GeneTorrent™ download application 1624, which executes on the SRDC download client 1546 at a GDAC 1516. In one embodiment the sequence data files are transferred between the GeneTorrent™ clients on the SRDC 1510 and a GDAC by way of bi-directionally authenticated SSL sessions over TCP/IP.

File Submission

In an exemplary embodiment Analysis objects are the primary container for submitting and downloading sequence data. Each Analysis object may include one or binary sequence Alignment/Mapping (BAM) files and is associated with an XML metadata file. The payload of each BAM file contains both the sequencing data (in bases, quality scores, and read names produced by the sequencing instrument) and read placements with annotations about strand, alignment, and quality features. Raw sequence read files, such as .srf files, can also be submitted along with the BAM files. In the exemplary embodiment each data submission includes a file of submission metadata compliant with the SRA 1.3 XML schema.

When making a new data submission a user will create and save a user authentication key via an authentication Web page hosted by or in association with the SRDC 1510. The user may then invoke an application on the SRDC client 1540 to create a unique identifier (UUID) to associate with the Analysis object. Assigning a UUID to the Analysis object ensures that the submission can be subsequently uniquely identified relative to all other submissions provided to the SRDC 1510. The user may then create a directory on the SRDC client 1540 and copy the XML metadata file (e.g., "analysis.xml") and sequence data files relating to the Analysis object into the directory. In one embodiment such sequence data files may include additional files of type other than BAM, such as legacy formats or proprietary formats containing raw read data. For example, the RNA-seq raw read data could be submitted along with the alignment data in the BAM. In one embodiment these additional files will be uploaded, stored and downloaded along with the BAM file as part of the same Analysis object.

In one embodiment the SRDC 1510 maintains a list of users permitted to upload new submission sequence and metadata. This list may be maintained by, for example, an out-of-band interaction between personnel representing each GSC 1514 and operations staff of the SRDC 1510. Specifically, the user name (and optionally a project group) will be identified within the SRDC 1510 as the owner(s) of the associated sequence data files. This enables a check to be performed during the submission process to confirm that the user's group membership matches or is otherwise appropriately associated with the GSC 1514 from which the submission is being received (e.g. users associated with GSC "BI" can only submit metadata for centername="BI"). If a user requests modification or suppression of a submission (thereby making the associated sequence data file(s) unavailable for download), the SRDC 1510 will verify that the user is a member of the group that owns that submission.

Once a user has been authenticated (i.e. proven to be who they say they are), access to sequence data may be further constrained by applicable project consent authorization constraints. For example, consents from owners of sequence data relating to those users eligible to download such data may be received by the SRDC 1510 in one or more files on a regular (e.g., daily) basis. The SRDC 1510 may then update one or more internal authorization tables to reflect any changes. In one embodiment each file of sequence data within the repository 1545 is associated with a project coordinated by the DCC 1512 through the identifier (e.g., UUID) assigned to the biospecimen from which the sequence data file was derived. The SRDC 1510 may receive this tag as part of the sequence data submission process. In one embodiment the SRDC 1510 may then confirm with the DCC 1512 that the identifier is valid. The DCC 1512 may also provide information on whether the sample has been redacted.

File Upload

As is discussed below, uploading of a new submission of sequence-related data generally involves several operations.

First, the user at the applicable GSC is authenticated and the submission "package" of files to be uploaded is validated. Next, the Analysis object with associated metadata is added to a repository catalog associated with one or both of the applicable DCC 1512 and the SDRC 1510. The set of one or more sequence data files included within the submission package are then transferred to the SDRC 1510. The correctness of the transfer may then be verified, and its legitimacy may be confirmed with reference to information maintained within the DCC 1512. The upload process is then generally concluded by setting appropriate authorizations for access to the information within the new Analysis object.

During an upload session, a user will typically transfer a plurality of files related to sequencing of a sample to the SRDC 1510. For example, in one embodiment these files, which are all associated with the same Analysis object, may include one or more XML files containing metadata about the sequence data files of interest. The Analysis object may, but need not, also include one or more sequence data files (e.g., BAM files) associated with the metadata.

In one embodiment the GeneTorrent™ upload client 1620 will first pass the XML metadata files of the Analysis object to the SRDC 1510, where consistency checks and other types of validation will be performed (stage 1550). During this stage all necessary validation is performed in order to ensure that the metadata and BAM file headers are complete and correctly formatted. The SRDC 1510 will validate the structural metadata required to identify and manage the sequencing data and may also perform any project-specific validation rules required to ensure consistency between the metadata and BAM headers. In the event such validation is successful, a metadata client module of the SRDC client 1540 will generate a manifest.xml file that can be passed to the GeneTorrent™ client 1620 for use in uploading the sequence data files of the Analysis object to the SRDC 1510 (stage 1548). In the event that errors are found in the submission, in one embodiment a complete error log will be returned with descriptive errors to help isolate the failures. If desired, a REST-based validation resource can be repeatedly invoked by the SRDC client 1540 through calls to the API provided by the Web Services 1614 in order to validate that the submission metadata is complete and accurate prior to submission.

If the metadata upload is successful, the GeneTorrent™ client 1620 will locate all of the sequence data file(s) (e.g., BAM file(s)) listed in the analysis.xml file within the directory created during the submission stage. Next, the GeneTorrent™ client 1620 will connect to the API provided by the Web Services 1614 and pass a GeneTorrent™ object file ("GTO"), which is used by the GTO Executive™ subsystem 1606 to initiate the upload. The GTO Executive™ subsystem 1606 will identify the address of the upload user and generate the required digital certificates. Once this has occurred the GTO Executive™ subsystem 1606 will spawn multiple GeneTorrent™ upload actor instances, which will begin uploading a first of the one or more sequence data files listed in the analysis.xml file. In particular, the GeneTorrent™ upload client 1620 then segments the file and begins parallel file transfer sessions of the file pieces over SSL. The GeneTorrent™ protocol will manage transmissions errors on any of the file pieces and will reassemble the file at the SDRC 1510.

Once the transfer is complete, the SRDC 1510 will perform a series of validation steps prior to making the data available for download. In one embodiment these steps may include, for example, computing the MD5 checksum and comparing it against the value in the XML metadata file, verifying the name of the transferred sequence data file matches the name in the XML metadata file, and validating that the headers of the transferred sequence data file match the header information in the XML metadata file. In one embodiment the DCC 1512 will be queried to determine if the sample is valid and is in an active state (e.g. has not been redacted). If the sample cannot be found, the state will be set to "verifying sample". If the sample is found, but has been redacted, the state will be set to "suppressed". In both cases, the SDRC 1510 will periodically poll the DCC 1512 to see if the state has changed.

The GeneTorrent™ application 1608 will optionally calculate an MD5 checksum for each file and validate that it matches the MD5 checksum in the manifest XML to confirm that it has the right files before transferring the data. Once all of the validation succeeds, the submission state becomes "live" and the Analysis object is available for download. The SDRC 1510 will continue to periodically poll the DCC 1512 for all live samples and will suppress all Analysis objects associated with samples that have been redacted.

During the process of submitting metadata as well as during sequence data upload process initiated by the GeneTorrent™ client 1620, the user may utilize a query tool provided by the SRDC client 1540 to monitor the submission status and determine when the upload and validation processing is complete. Alternatively, this monitoring may be effected by directly accessing the REST Web Services 1614.

For upload operations, the GeneTorrent™ client 1620 will take command line parameters for user authentication along with a sequence data submission described by an associated XML metadata file. One or more sequence files specified by the metadata file are then packaged into an Analysis Object. The GeneTorrent™ client 1620 will generally be configured to display the progress of the upload of the Analysis Object. Users will also be able to query an API associated with a REST Web services module 1628 within the GTO Executive™ subsystem 1606 to independently monitor status of the submission.

In summary, at least the following are included among the methods and systems for secure, high-speed file transfer of very large files disclosed herein:

A method for transmitting (e.g., at >10 Gbits speed) BAM and xml files from an optical network to storage arrays using a client configured to transmit parallel streams of a file to a switch (e.g., a 10 Gbits switch) capable of sending different portions of the file to multiple file servers running the same file transfer application. A second switch may also be provided for high-speed access to multiple storage clusters.

A method for storing genome sequence files and metadata files that render them searchable by any attribute that is a field in the header or xml file An apparatus for receiving a high-speed transmission of parallelized bit streams and evenly distributing the large file transfer across a series of application servers through a high speed switch.

A method for monitoring the patient consent status and the authorized user of such phenotypic and genomic data.

A method of formatting genomic data with the germline variants data stored in one layer of a data model while somatic mutation data are stored in a different layer of the data model.

A method for storing a particular set of molecular data that is associated with a certain disease separately from other molecular expression data and variants data that is associated with other diseases.

A method for the initiating the high-speed transfer of genomic data by configuring a client program at a genome sequencing center to prompt a data repository to receive a highly-parallelized transfer of genome data.

A method for encryption of genome data in layers to make the data accessible based upon multiple levels of sensitivity.

A method for encrypting genome sequence data wherein at least one layer consists of validated germline mutation call, repeat sequences and genotyping variants data.

A method for encrypting genome sequence data wherein at least one layer of encryption consist of validate somatic mutations found in the genome of tissue/cell of a tumor.

A method for encrypting genome sequence data wherein at least one layer of encryption consist of validate somatic mutations found in the genome of diseased tissue such as brain.

A method for encryption of transcriptome sequence data in layers to make the data accessible based upon multiple levels of sensitivity.

A method for encrypting transcriptome sequence data wherein at least one layer consist of validated germline mutation call, repeat sequences and other genotyping variants data.

A method for encrypting transcriptome sequence data wherein at least one layer of encryption consist of validate somatic mutations found in the genome of tissue/cell of a tumor.

A method for encrypting transcriptome sequence data wherein at least one layer of encryption consist of validate somatic mutations found in the genome of diseased tissue such as brain.

A method to encrypt ancillary data associated any biological sequence data in a configuration consistent any combination of information types.

An entitlement control system that uses data owner consent and user authorization to regulate transactions involving sequence data.

A method of using a highly distributed conditional access system to secure biological sequence and related data files.

A method for using a highly distributed conditional access system to regulate the access to data between at least two transaction points.

A method for encoding biological sequence data files to grant conditional access based on user consent.

A method to control and coordinate secure transactions by distribution of public/private keys for use with GeneTorrent™ technology configured to send parallelized data streams from a source actor to a destination.

A method to transmit multiple secure instances of a single Gene Torrent Object (GTO) file over parallel streams. The method includes using software clients for uploading and downloading the genome data files. The method may include authorizing a user's request to download a particular file based upon, for example, the consent of the file owner to a transfer of the file. The method may further contemplate that encryption keys are exchanged between trusted partners on the network for security.

A process for configuring a single biological data file as multiple instances on more than one server and transmitting the file to one or more network nodes.

A method of entitlement control that allows parallel streams of one universally identifiable GeneTorrent™ file from more than one actors to more than one node on a network based on static and dynamic consent rules.

A computer-implemented process that accepts binary alignment map or a related formatted biological sequence data file and transmits it over a network in multiple parallel instances.

Specific details are given in the above description to provide a thorough understanding of the embodiments. However, it is understood that the embodiments may be practiced without these specific details. For example, circuits or other apparatus may be shown in block diagrams in order not to obscure the embodiments in unnecessary detail. In other instances, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, virtualization systems or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure. It is intended that the following claims and their equivalents define the scope of the systems and methods described herein.

We claim:

1. A method for facilitating transfer of an electronic file over a network, the method comprising:
   sending a first portion of the electronic file from a first server instance of a plurality of server instances;
   sending a second portion of the electronic file from a second server instance of the plurality of server instances;
   receiving, at the first server instance, information relating to the second portion of the electronic file sent by the second server instance; and
   sending a third portion of the electronic file from the first server instance;
   wherein the third portion is different from the second portion and wherein the first portion, the second portion and the third portion of the electronic file are included within parallel data streams sent by the first server instance and the second server instance.

2. The method of claim 1 further including reading the first portion of the electronic file from a database containing the electronic file.

3. The method of claim 2 further including reading the third portion of the electronic file from the database.

4. The method of claim 1 further including providing, to the second server instance, information relating to the sending of the first portion of the electronic file.

5. The method of claim 1 further including receiving information relating to a fourth portion of the electronic file sent by a third server instance wherein the third portion is different from the fourth portion.

6. The method of claim 5 further including sending, from the first server instance, a fifth portion of the electronic file wherein the fifth portion is different from the second portion and the fourth portion.

7. The method of claim 1 wherein the first portion of the electronic file is sent to a first receiving node different from a second receiving node configured to receive the second portion of the electronic file.

8. The method of claim 1 wherein the third portion of the electronic file is sent to the first receiving node.

9. The method of claim 1 further including:
   receiving information relating to corruption of the first portion of the electronic file; and
   resending the first portion of the electronic file from the first server instance.

10. The method of claim 1 wherein the electronic file includes genomic information.

11. The method of claim 10 wherein the genomic information comprises information associated with a plurality of layers of a data model.

12. The method of claim 11 wherein the first portion, the second portion and the third portion of the electronic data file are each associated with a first of the plurality of layers.

13. The method of claim 11 wherein the first portion of the electronic file is associated with a first of the plurality of layers and the second portion of the electronic file is associated with a second of the plurality of layers.

14. A method for facilitating transfer of an electronic file over a network, the method comprising:
   generating first encrypted file information by encrypting a first portion of the electronic file using first encryption information;
   generating second encrypted file information by encrypting a second portion of the electronic file using second encryption information different from the first encryption information;
   generating third encrypted file information by encrypting a third portion of the electronic file using the first encryption information;
   sending, from a first server instance, a data stream including the first encrypted file information and the third encrypted file information and
   sending the second encrypted file information from a second server instance;
   wherein the first encrypted file information, the second encrypted file information and the third encrypted file information are included within parallel data streams sent by the first server instance and the second server instance.

15. The method of claim 14 wherein the first encryption information includes a first encryption key and the second encryption information includes a second encryption key.

16. The method of claim 14 wherein the electronic file includes genomic information.

17. The method of claim 16 wherein the genomic information comprises information associated with a plurality of layers of a data model.

18. A method for facilitating transfer of an electronic file over a network, the method comprising:
   receiving, from a first receiving node, a first portion of an electronic file sent by a first sending node;
   receiving, from a second receiving node, a second portion of the electronic file sent by a second sending node; and
   receiving, from the first receiving node, a third portion of the electronic file sent by the first sending node wherein the first portion, the second portion and the third portion of the electronic file are included within parallel data streams received by the first receiving node and the second receiving node.

19. The method of claim 18 wherein the first portion of the electronic file is encrypted using first encryption information and is associated with a first layer of a plurality of layers of information within the electronic file and wherein the second portion of the electronic file is encrypted using second encryption information and is associated with a second layer of the plurality of layers of information within the electronic file.

20. The method of claim 18 wherein the first portion of the electronic file is encrypted using first encryption information and the second portion of the electronic file is encrypted using second encryption information, the first receiving node and the second receiving node being located within a user system.

21. The method of claim 1 wherein the first sending node and the second sending node are located within a genome data repository.

22. A method for facilitating transfer of an electronic file over a network, the method comprising:
   receiving a request for the electronic file;
   creating multiple server instances for use in downloading the electronic file, wherein the multiple server instances include a first sending node and a second sending node;
   encrypting a first portion of the electronic file, a second portion of the electronic file and a third portion of the electronic file wherein the first portion of the electronic file is different than the second portion of the electronic file and the third portion of the electronic file is different from the first portion of the electronic file and the second portion of the electronic file;
   sending, after the encrypting, the encrypted first portion of the electronic file and the encrypted third portion of the electronic file in a data stream from the first sending node; and
   sending, after the encrypting, the encrypted second portion of the electronic file from the second sending node.

23. The method of claim 22 wherein the first sending node and the second sending node are located within a genome data repository.

24. The method of claim 22 wherein the sending the first encrypted portion of the electronic file and the sending the second encrypted portion of the electronic file are performed in parallel.

25. The method of claim 1 wherein the first portion of the electronic file and the second portion of the electronic file are sent in parallel.

* * * * *